(12) United States Patent
Greul et al.

(10) Patent No.: US 8,921,575 B2
(45) Date of Patent: Dec. 30, 2014

(54) O-CYCLOPROPYLCYCLOHEXYL-CARBOXANILIDES AND THEIR USE AS FUNGICIDES

(71) Applicant: Bayer Intellectual Property GmbH, Monheim (DE)

(72) Inventors: Joerg Nico Greul, Leverkusen (DE); Juergen Benting, Leichlingen (DE); Peter Dahmen, Neuss (DE); Ulrike Wachendorff-Neumann, Neuwied (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 14/089,367

(22) Filed: Nov. 25, 2013

(65) Prior Publication Data
US 2014/0081030 A1    Mar. 20, 2014

Related U.S. Application Data

(62) Division of application No. 13/701,403, filed as application No. PCT/EP2011/059005 on Jun. 1, 2011, now Pat. No. 8,653,114.

(60) Provisional application No. 61/368,003, filed on Jul. 27, 2010.

(30) Foreign Application Priority Data

| Jun. 3, 2010 | (EP) | 10356020 |
| Nov. 15, 2010 | (EP) | 10191262 |
| Nov. 15, 2010 | (EP) | 10356032 |

(51) Int. Cl.
| C07D 231/16 | (2006.01) |
| C07D 231/18 | (2006.01) |
| A01N 37/18 | (2006.01) |
| A01N 43/40 | (2006.01) |
| A01N 43/56 | (2006.01) |
| A01N 43/80 | (2006.01) |
| C07C 211/35 | (2006.01) |
| C07C 233/65 | (2006.01) |
| C07D 213/82 | (2006.01) |
| C07D 277/56 | (2006.01) |
| A01N 43/50 | (2006.01) |
| A01N 37/44 | (2006.01) |
| A01N 43/78 | (2006.01) |
| C07C 237/00 | (2006.01) |
| C07D 211/04 | (2006.01) |
| C07D 231/14 | (2006.01) |
| C07D 277/02 | (2006.01) |
| C07D 231/12 | (2006.01) |

(52) U.S. Cl.
CPC .............. *C07D 231/18* (2013.01); *A01N 37/18* (2013.01); *A01N 43/40* (2013.01); *A01N 43/56* (2013.01); *A01N 43/80* (2013.01); *C07C 211/35* (2013.01); *C07C 233/65* (2013.01); *C07D 213/82* (2013.01); *C07D 231/16* (2013.01); *C07D 277/56* (2013.01); *A01N 43/50* (2013.01); *A01N 37/44* (2013.01); *A01N 43/78* (2013.01); *C07C 237/00* (2013.01); *C07D 211/04* (2013.01); *C07D 231/14* (2013.01); *C07D 277/02* (2013.01); *C07D 231/12* (2013.01); *C07C 2101/02* (2013.01); *C07C 2101/14* (2013.01)
USPC ..................................................... 548/374.1

(58) Field of Classification Search
CPC ..................................................... C07D 231/16
See application file for complete search history.

(56) References Cited

U.S. PATENT DOCUMENTS

| 6,462,049 | B1 * | 10/2002 | Ogura et al. | 514/254.02 |
| 7,037,880 | B2 * | 5/2006 | Ogura et al. | 504/155 |
| 7,566,683 | B2 * | 7/2009 | Ogura et al. | 504/238 |
| 8,344,015 | B2 | 1/2013 | Dunkel et al. | |

FOREIGN PATENT DOCUMENTS

| EP | 2251331 | 11/2010 |
| WO | 03074491 | 9/2003 |

OTHER PUBLICATIONS

Patani et al. (Chem. Rev. 1996, 3147-3176).*
International Search Report for PCT/EP2011/059005 Mailed Aug. 29, 2011.

* cited by examiner

*Primary Examiner* — Kamal Saeed
(74) *Attorney, Agent, or Firm* — Miles & Stockbridge P.C.

(57) ABSTRACT

The present invention relates to O-CYCLOPROPYLCY-CLOHEXYL-CARBOXANILIDES derivatives of formula (I); their process of preparation, their use as fungicide, particularly in the form of fungicide compositions, and methods for the control of phytopathogenic fungi, notably of plants, using these compounds or compositions.

7 Claims, No Drawings

O-CYCLOPROPYLCYCLOHEXYL-CARBOXANILIDES AND THEIR USE AS FUNGICIDES

CROSS REFERENCE TO RELATED APPLICATIONS

This application is a Divisional Application of U.S. application Ser. No. 13/701,403, filed Feb. 6, 2013, which is a §371 National Stage Application of PCT/EP2011/059055, filed Jun. 1, 2011, which claims priority to European Application No. 10356020.7, filed Jun. 3, 2010, U.S. Provisional Application No. 61/368,003, filed Jul. 27, 2010, European Application No. 10356032.2, filed Nov. 15, 2010, and European Application No. 10191262.4, filed Nov. 15, 2010, the content of all of which are herein incorporated by reference in their entireties.

BACKGROUND

1. Field of the Invention

The present invention relates to novel ortho-substituted cyclopropylcyclohexyl carboxamide which have microbiocidal activity, in particular fungicidal activity. The invention also relates to the preparation of these compounds, to novel intermediates used in the preparation of these compounds, to agrochemical compositions which comprise at least one of the novel compounds as active ingredient, to the preparation of the compositions mentioned and to the use of the active ingredients or compositions in agriculture or horticulture for controlling or preventing infestation of plants by phytopathogenic microorganisms, preferably fungi.

2. Description of Related Art

WO-A 2003/074491 discloses certain ortho-unsubstituted-cyclopropyl-phenyl-carboxamides:

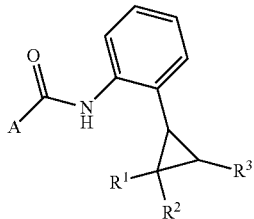

SUMMARY

The present invention provides ortho-substituted cyclopropylcyclohexyl carboxamide compounds of formula (I) which are new:

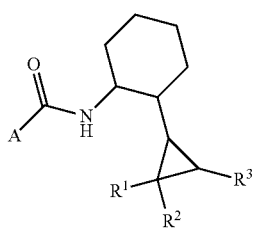

(I)

in which $R^1$ represents hydrogen, fluoro, chloro or bromo;

$R^2$ represents hydrogen fluoro, chloro or bromo;

$R^3$ represents optionally substituted $C_{2-12}$ alkyl, optionally substituted $C_{2-12}$ alkenyl, optionally substituted $C_{2-12}$ alkynyl, optionally substituted $C_{3-12}$ cycloalkyl, optionally substituted phenyl or optionally substituted heterocyclyl;

A represents one of the radicals A1 to A18 below

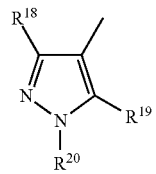

A1

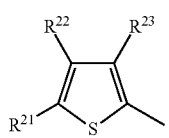

A2

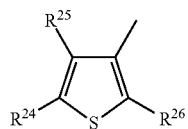

A3

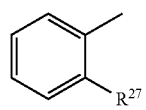

A4

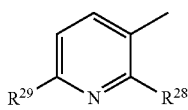

A5

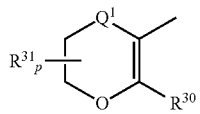

A6

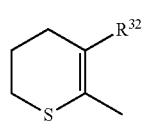

A7

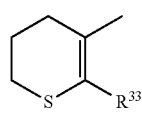

A8

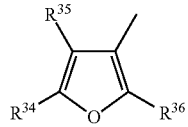

A9

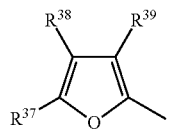

A10

A11 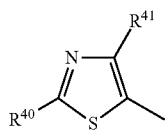

A12 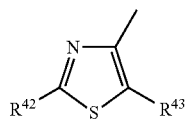

A13 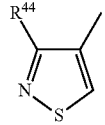

A14 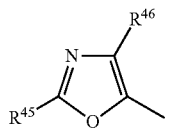

A15 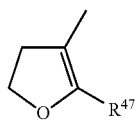

A16 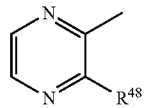

A17 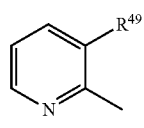

A18 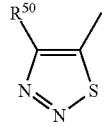

$R^{18}$ represents hydrogen, cyano, halogen, nitro, $C_1$-$C_4$-alkyl, $C_1$-$C_4$-alkoxy, $C_1$-$C_4$-alkylthio, $C_3$-$C_6$-cycloalkyl, $C_1$-$C_4$-haloalkyl, $C_1$-$C_4$-haloalkoxy or $C_1$-$C_4$-haloalkylthio having in each case 1 to 5 halogen atoms, aminocarbonyl or aminocarbonyl-$C_1$-$C_4$-alkyl, $R^{19}$ represents hydrogen, halogen, cyano, $C_1$-$C_4$-alkyl, $C_1$-$C_4$-alkoxy or $C_1$-$C_4$-alkylthio, $R^{20}$ represents hydrogen, $C_1$-$C_4$-alkyl, hydroxy-$C_1$-$C_4$-alkyl, $C_2$-$C_6$-alkenyl, $C_3$-$C_6$-cycloalkyl, $C_1$-$C_4$-alkylthio-$C_1$-$C_4$-alkyl, $C_1$-$C_4$-alkoxy-$C_1$-$C_4$-alkyl, $C_1$-$C_4$-haloalkyl, $C_1$-$C_4$-haloalkylthio-$C_1$-$C_4$-alkyl, $C_1$-$C_4$-haloalkoxy-$C_1$-$C_4$-alkyl having in each case 1 to 5 halogen atoms, or phenyl, $R^{21}$ and $R^{22}$ independently of one another represent hydrogen, halogen, $C_1$-$C_4$-alkyl or $C_1$-$C_4$-haloalkyl having 1 to 5 halogen atoms, $R^{23}$ represents halogen, cyano or $C_1$-$C_4$-alkyl, or $C_1$-$C_4$-haloalkyl or $C_1$-$C_4$-haloalkoxy having in each case 1 to 5 halogen atoms, $R^{24}$ and $R^{25}$ independently of one another represent hydrogen, halogen, $C_1$-$C_4$-alkyl or $C_1$-$C_4$-haloalkyl having 1 to 5 halogen atoms, $R^{26}$ represents hydrogen, halogen, $C_1$-$C_4$-alkyl or $C_1$-$C_4$-haloalkyl having 1 to 5 halogen atoms, $R^{27}$ represents hydrogen, halogen, hydroxyl, cyano, $C_1$-$C_6$-alkyl, $C_1$-$C_4$-haloalkyl, $C_1$-$C_4$-haloalkoxy or $C_1$-$C_4$-haloalkylthio having in each case 1 to 5 halogen atoms, $R^{28}$ represents halogen, hydroxyl, cyano, $C_1$-$C_4$-alkyl, $C_1$-$C_4$-alkoxy, $C_1$-$C_4$-alkylthio, $C_1$-$C_4$-haloalkyl, $C_1$-$C_4$-haloalkylthio or $C_1$-$C_4$-haloalkoxy having in each case 1 to 5 halogen atoms, $R^{29}$ represents hydrogen, halogen, cyano, $C_1$-$C_4$-alkyl, $C_1$-$C_4$-alkoxy, $C_1$-$C_4$-alkylthio, $C_1$-$C_4$-haloalkyl, $C_1$-$C_4$-haloalkoxy having in each case 1 to 5 halogen atoms, $C_1$-$C_4$-alkylsulphinyl or $C_1$-$C_4$-alkylsulphonyl, $R^{30}$ represents $C_1$-$C_4$-alkyl or $C_1$-$C_4$-haloalkyl having 1 to 5 halogen atoms, $R^{31}$ represents $C_1$-$C_4$-alkyl, $Q^1$ represents S (sulphur), SO, $SO_2$ or $CH_2$, p represents 0, 1 or 2, where $R^{31}$ represents identical or different radicals if p represents 2, $R^{32}$ represents $C_1$-$C_4$-alkyl or $C_1$-$C_4$-haloalkyl having 1 to 5 halogen atoms, $R^{33}$ represents $C_1$-$C_4$-alkyl or $C_1$-$C_4$-haloalkyl having 1 to 5 halogen atoms, $R^{34}$ and $R^{35}$ independently of one another represent hydrogen, halogen, amino, $C_1$-$C_4$-alkyl or $C_1$-$C_4$-haloalkyl having 1 to 5 halogen atoms, $R^{36}$ represents hydrogen, halogen, $C_1$-$C_4$-alkyl or $C_1$-$C_4$-haloalkyl having 1 to 5 halogen atoms, $R^{37}$ and $R^{38}$ independently of one another represent hydrogen, halogen, amino, nitro, $C_1$-$C_4$-alkyl or $C_1$-$C_4$-haloalkyl having 1 to 5 halogen atoms, $R^{39}$ represents hydrogen, halogen, $C_1$-$C_4$-alkyl or $C_1$-$C_4$-haloalkyl having 1 to 5 halogen atoms, $R^{40}$ represents hydrogen, halogen, amino, $C_1$-$C_4$-alkylamino, di-($C_1$-$C_4$-alkyl)amino, cyano, $C_1$-$C_4$-alkyl or $C_1$-$C_4$-haloalkyl having 1 to 5 halogen atoms, $R^{41}$ represents halogen, $C_1$-$C_4$-alkyl or $C_1$-$C_4$-haloalkyl having 1 to 5 halogen atoms, $R^{42}$ represents hydrogen, halogen, amino, $C_1$-$C_4$-alkylamino, di-($C_1$-$C_4$-alkyl)amino, cyano, $C_1$-$C_4$-alkyl or $C_1$-$C_4$-haloalkyl having 1 to 5 halogen atoms, $R^{43}$ represents halogen, $C_1$-$C_4$-alkyl or $C_1$-$C_4$-haloalkyl having 1 to 5 halogen atoms, $R^{44}$ represents halogen, $C_1$-$C_4$-alkyl or $C_1$-$C_4$-haloalkyl having 1 to 5 halogen atoms, $R^{45}$ represents hydrogen or $C_1$-$C_4$-alkyl, $R^{46}$ represents halogen or $C_1$-$C_4$-alkyl, $R^{47}$ represents $C_1$-$C_4$-alkyl or $C_1$-$C_4$-haloalkyl having 1 to 5 halogen atoms, $R^{48}$ represents hydrogen, halogen, $C_1$-$C_4$-alkyl or $C_1$-$C_4$-haloalkyl having 1 to 5 halogen atoms, $R^{49}$ represents halogen, hydroxyl, $C_1$-$C_4$-alkyl, $C_1$-$C_4$-alkoxy, $C_1$-$C_4$-alkylthio, $C_1$-$C_4$-haloalkyl, $C_1$-$C_4$-haloalkylthio or $C_1$-$C_4$-haloalkoxy having in each case 1 to 5 halogen atoms, $R^{50}$ represents $C_1$-$C_4$-alkyl;

Each alkyl moiety is a straight or branched chain and is, for example, methyl, ethyl, n-propyl, n-butyl, n-pentyl, n-hexyl, iso-propyl, n-butyl, sec-butyl, iso-butyl, tert-butyl or neopentyl.

When present, each optional substituent on an alkyl moiety is, independently, selected from halo, hydroxy, cyano, $C_{1-4}$ alkoxy C(=O), formyl, nitro, $C_{1-4}$ alkoxy, $C_{1-4}$ haloalkoxy, $C_{1-4}$ alkylthio, $C_{1-4}$ haloalkylthio.

Alkenyl and alkynyl moieties can be in the form of straight or branched chains. The alkenyl moieties, where appropriate, can be of either the (E)- or (Z)-configuration. Examples are vinyl, allyl and propargyl.

When present, each optional substituent on alkenyl or on alkynyl is, independently, selected from those optional substituents given above for an alkyl moiety.

Cycloalkyl includes cyclopropyl, cyclobutyl, cyclopentyl and cyclohexyl.

When present, each optional substituent on cycloalkyl is, independently, selected from $C_{1-3}$ alkyl and those optional substituents given above for an alkyl moiety.

The term heterocyclyl refers to a non-aromatic or aromatic ring containing up to 10 atoms including one or more (preferably one or two) heteroatoms selected, each independently, from O, S and N. Examples of such rings include 1,3-dioxolanyl, tetrahydrofuranyl, morpholinyl, thienyl and furyl.

When present, each optional substituent on phenyl or on heterocyclyl is, independently, selected from $C_{1-6}$ alkyl and those optional substituents given above for an alkyl moiety. When present, there are up to four optional substituents on phenyl, each independently selected.

When present, each optional substituent on an alkyl moiety is, independently, selected from the preferred list of halo, hydroxy, methoxy, trifluoromethoxy, difluoromethoxy, cyano and nitro.

When present, each optional substituent on alkenyl or on alkynyl is, independently, selected from the preferred list of halo and cyano.

When present, each optional substituent on cycloalkyl is, independently, selected from the preferred list of methyl, ethyl, trifluoromethyl, methoxy, trifluoromethoxy and cyano.

When present, each optional substituent on phenyl or on a heterocyclyl group is, independently, selected from the preferred list of halo, hydroxy, methoxy, trifluoromethoxy, difluoromethoxy and cyano.

DETAILED DESCRIPTION OF A PREFERRED EMBODIMENT $R^1$ and $R^2$ preferably are, independently, hydrogen or fluoro.
$R^1$ and $R^2$ particularly preferably are hydrogen.
$R^3$ preferably is $C_{2-6}$ alkyl, optionally substituted $C_{3-8}$ cycloalkyl, phenyl, thienyl or furyl.
$R^3$ particularly preferably is $C_{2-6}$ alkyl, optionally substituted $C_{3-8}$ cycloalkyl.
$R^3$ very particularly preferably is $C_{2-6}$ alkyl, optionally substituted cyclopropyl.
A particularly preferably represents one of the radicals A1, A2, A3, A4, A5, A6, A9, A10, A11, A12 or A17.
A particularly preferably represents one of the radicals A1, A2, A4, A5, A6, A9, A11, A12, A16, A17.
A very particularly preferably represents one of the radicals A1, A2, A4, A5, A11, A12, A16, A17.
A very particularly preferably represents the radical A1.
A furthermore very particularly preferably represents the radical A2.
A furthermore very particularly preferably represents the radical A4.
A furthermore very particularly preferably represents the radical A5.
A furthermore very particularly preferably represents the radical A6.
A furthermore very particularly preferably represents the radical A9.
A furthermore very particularly preferably represents the radical A11.
A furthermore very particularly preferably represents the radical A12.
A furthermore very particularly preferably represents the radical A16.
A furthermore very particularly preferably represents the radical A17.
$R^{18}$ preferably represents hydrogen, cyano, fluorine, chlorine, bromine, iodine, methyl, ethyl, isopropyl, methoxy, ethoxy, methylthio, ethylthio, cyclopropyl, $C_1$-$C_2$-haloalkyl, $C_1$-$C_2$-haloalkoxy having in each case 1 to 5 fluorine, chlorine and/or bromine atoms, trifluoromethylthio, difluoromethylthio, aminocarbonyl, aminocarbonylmethyl or aminocarbonylethyl.
$R^{18}$ particularly preferably represents hydrogen, fluorine, chlorine, bromine, iodine, methyl, ethyl, isopropyl, monofluoromethyl, monofluoroethyl, difluoromethyl, trifluoromethyl, difluorochloromethyl, trichloromethyl, dichloromethyl, cyclopropyl, methoxy, ethoxy, trifluoromethoxy, trichloromethoxy, methylthio, ethylthio, trifluoromethylthio or difluoromethylthio.
$R^{18}$ very particularly preferably represents hydrogen, fluorine, chlorine, bromine, iodine, methyl, isopropyl, monofluoromethyl, monofluoroethyl, difluoromethyl, trifluoromethyl, difluorochloromethyl, dichloromethyl or trichloromethyl.
$R^{18}$ especially preferably represents methyl, difluoromethyl, trifluoromethyl, dichloromethyl or 1-fluoroethyl.
$R^{18}$ especially very preferably represents difluoromethyl or dichloromethyl.
$R^{19}$ preferably represents hydrogen, fluorine, chlorine, bromine, iodine, methyl, ethyl, methoxy, ethoxy, methylthio or ethylthio.
$R^{19}$ particularly preferably represents hydrogen, fluorine, chlorine, bromine, iodine or methyl.
$R^{19}$ very particularly preferably represents hydrogen, fluorine, chlorine or methyl.
$R^{19}$ especially preferably represents fluorine, chlorine.
$R^{20}$ preferably represents hydrogen, methyl, ethyl, n-propyl, isopropyl, $C_1$-$C_2$-haloalkyl having 1 to 5 fluorine, chlorine and/or bromine atoms, hydroxymethyl, hydroxyethyl, cyclopropyl, cyclopentyl, cyclohexyl or phenyl.
$R^{20}$ particularly preferably represents hydrogen, methyl, ethyl, isopropyl, trifluoromethyl, difluoromethyl, hydroxymethyl, hydroxyethyl or phenyl.
$R^{20}$ very particularly preferably represents hydrogen, methyl, trifluoromethyl or phenyl.
$R^{20}$ especially preferably represents methyl.

Particularly preferred are compounds according to formula (I) wherein $R^{18}$ is difluoromethyl or dichloromethyl, $R^{19}$ is fluorine or chlorine, and $R^{20}$ is methyl.

Particularly preferred are compounds according to formula (I) wherein $R^{18}$ is difluoromethyl, $R^{19}$ is fluorine, and $R^{20}$ is methyl.

$R^{21}$ and $R^{22}$ independently of one another preferably represent hydrogen, fluorine, chlorine, bromine, methyl, ethyl or $C_1$-$C_2$-haloalkyl having 1 to 5 fluorine, chlorine and/or bromine atoms.
$R^{21}$ and $R^{22}$ independently of one another particularly preferably represent hydrogen, fluorine, chlorine, bromine, methyl, ethyl, difluoromethyl, trifluoromethyl, difluorochloromethyl or trichloromethyl.
$R^{21}$ and $R^{22}$ independently of one another very particularly preferably represent hydrogen, fluorine, chlorine, bromine, methyl, ethyl, difluoromethyl, trifluoromethyl or trichloromethyl.
$R^{21}$ and $R^{22}$ especially preferably each represent hydrogen.

$R^{23}$ preferably represents fluorine, chlorine, bromine, cyano, methyl, ethyl, $C_1$-$C_2$-haloalkyl or $C_1$-$C_2$-haloalkoxy having in each case 1 to 5 fluorine, chlorine and/or bromine atoms.

$R^{23}$ particularly preferably represents fluorine, chlorine, bromine, cyano, methyl, trifluoromethyl, trifluoromethoxy, difluoromethoxy, difluorochloromethoxy or trichloromethoxy.

$R^{23}$ very particularly preferably represents fluorine, chlorine, bromine, iodine, methyl, trifluoromethyl or trifluoromethoxy.

$R^{23}$ especially preferably represents methyl or trifluoromethyl.

$R^{24}$ and $R^{25}$ independently of one another preferably represent hydrogen, fluorine, chlorine, bromine, methyl, ethyl or $C_1$-$C_2$-haloalkyl having 1 to 5 fluorine, chlorine and/or bromine atoms.

$R^{24}$ and $R^{25}$ independently of one another particularly preferably represent hydrogen, fluorine, chlorine, bromine, methyl, ethyl, difluoromethyl, trifluoromethyl, difluorochloromethyl or trichloromethyl.

$R^{24}$ and $R^{25}$ independently of one another very particularly preferably represent hydrogen, fluorine, chlorine, bromine, methyl, ethyl, difluoromethyl, trifluoromethyl or trichloromethyl.

$R^{24}$ and $R^{25}$ especially preferably each represent hydrogen.

$R^{26}$ preferably represents hydrogen, fluorine, chlorine, bromine, iodine, methyl, ethyl or $C_1$-$C_2$-haloalkyl having 1 to 5 fluorine, chlorine and/or bromine atoms.

$R^{26}$ particularly preferably represents hydrogen, fluorine, chlorine, bromine, iodine, methyl or trifluoromethyl.

$R^{26}$ very particularly preferably represents fluorine, chlorine, bromine, iodine, methyl or trifluoromethyl.

$R^{27}$ preferably represents hydrogen, fluorine, chlorine, bromine, iodine, hydroxyl, cyano, $C_1$-$C_4$-alkyl, $C_1$-$C_2$-haloalkyl, $C_1$-$C_2$-haloalkoxy or $C_1$-$C_2$-haloalkylthio having in each case 1 to 5 fluorine, chlorine and/or bromine atoms.

$R^{27}$ particularly preferably represents hydrogen, fluorine, chlorine, bromine, iodine, hydroxyl, cyano, methyl, ethyl, n-propyl, isopropyl, n-butyl, isobutyl, sec-butyl, tert-butyl, difluoromethyl, trifluoromethyl, difluorochloromethyl, trichloromethyl, trifluoromethoxy, difluoromethoxy, difluorochloromethoxy, trichloromethoxy, trifluoromethylthio, difluoromethylthio, difluorochloromethylthio or trichloromethylthio.

$R^{27}$ very particularly preferably represents hydrogen, fluorine, chlorine, bromine, iodine, methyl, difluoromethyl, trifluoromethyl or trichloromethyl.

$R^{27}$ especially preferably represents iodine, methyl, difluoromethyl or trifluoromethyl.

$R^{28}$ preferably represents fluorine, chlorine, bromine, iodine, hydroxyl, cyano, $C_1$-$C_4$ alkyl, methoxy, ethoxy, methylthio, ethylthio, difluoromethylthio, trifluoromethylthio, $C_1$-$C_2$-haloalkyl or $C_1$-$C_2$-haloalkoxy having in each case 1 to 5 fluorine, chlorine and/or bromine atoms.

$R^{28}$ particularly preferably represents fluorine, chlorine, bromine, iodine, hydroxyl, cyano, methyl, ethyl, n-propyl, isopropyl, n-butyl, isobutyl, sec-butyl, tert-butyl, trifluoromethyl, difluoromethyl, difluorochloromethyl, trichloromethyl, methoxy, ethoxy, methylthio, ethylthio, difluoromethylthio, trifluoromethylthio, trifluoromethoxy, difluoromethoxy, difluorochloromethoxy or trichloromethoxy.

$R^{28}$ very particularly preferably represents fluorine, chlorine, bromine, iodine, methyl, trifluoromethyl, difluoromethyl or trichloromethyl.

$R^{29}$ preferably represents hydrogen, fluorine, chlorine, bromine, iodine, cyano, $C_1$-$C_4$ alkyl, methoxy, ethoxy, methylthio, ethylthio, $C_1$-$C_2$-haloalkyl or $C_1$-$C_2$-haloalkoxy having in each case 1 to 5 fluorine, chlorine and/or bromine atoms, $C_1$-$C_2$-alkylsulphinyl or $C_1$-$C_2$-alkyl sulphonyl.

$R^{29}$ particularly preferably represents hydrogen, fluorine, chlorine, bromine, iodine, cyano, n-propyl, isopropyl, n-butyl, isobutyl, sec-butyl, tert-butyl, trifluoromethyl, difluoromethyl, difluorochloromethyl, trichloromethyl, methoxy, ethoxy, methylthio, ethylthio, trifluoromethoxy, difluoromethoxy, difluorochloromethoxy, trichloromethoxy, methylsulphinyl or methylsulphonyl.

$R^{29}$ very particularly preferably represents hydrogen, fluorine, chlorine, bromine, iodine, n-propyl, isopropyl, n-butyl, isobutyl, sec-butyl, tert-butyl, trifluoromethyl, difluoromethyl, trichloromethyl, methylsulphinyl or methylsulphonyl.

$R^{29}$ especially preferably represents hydrogen.

$R^{30}$ preferably represents methyl, ethyl or $C_1$-$C_2$-haloalkyl having 1 to 5 fluorine, chlorine and/or bromine atoms.

$R^{30}$ particularly preferably represents methyl, ethyl, trifluoromethyl, difluoromethyl, difluorochloromethyl or trichloromethyl.

$R^{31}$ preferably represents methyl or ethyl.

$R^{31}$ particularly preferably represents methyl.

$Q^1$ preferably represents S (sulphur), SO or $CH_2$, p preferably represents 0 or 1, $R^{32}$ preferably represents methyl, ethyl or $C_1$-$C_2$-haloalkyl having 1 to 5 fluorine, chlorine and/or bromine atoms.

$R^{32}$ particularly preferably represents methyl, ethyl, trifluoromethyl, difluoromethyl, difluorochloromethyl or trichloromethyl.

$R^{32}$ very particularly preferably represents methyl, trifluoromethyl, difluoromethyl or trichloromethyl.

$R^{33}$ preferably represents methyl, ethyl or $C_1$-$C_2$-haloalkyl having 1 to 5 fluorine, chlorine and/or bromine atoms.

$R^{33}$ particularly preferably represents methyl, ethyl, trifluoromethyl, difluoromethyl, difluorochloromethyl or trichloromethyl.

$R^{33}$ very particularly preferably represents methyl, trifluoromethyl, difluoromethyl or trichloromethyl.

$R^{34}$ and $R^{35}$ independently of one another preferably represent hydrogen, fluorine, chlorine, bromine, amino, methyl, ethyl or $C_1$-$C_2$-haloalkyl having 1 to 5 fluorine, chlorine and/or bromine atoms.

$R^{34}$ and $R^{35}$ independently of one another particularly preferably represent hydrogen, fluorine, chlorine, bromine, methyl, ethyl, trifluoromethyl, difluoromethyl, difluorochloromethyl or trichloromethyl.

$R^{34}$ and $R^{35}$ independently of one another very particularly preferably represent hydrogen, fluorine, chlorine, bromine, methyl, trifluoromethyl, difluoromethyl or trichloromethyl.

$R^{34}$ and $R^{35}$ especially preferably each represent hydrogen.

$R^{36}$ preferably represents hydrogen, fluorine, chlorine, bromine, iodine, methyl, ethyl or $C_1$-$C_2$-haloalkyl having 1 to 5 fluorine, chlorine and/or bromine atoms.

$R^{36}$ particularly preferably represents hydrogen, fluorine, chlorine, bromine, iodine, methyl, ethyl, trifluoromethyl, difluoromethyl, difluorochloromethyl or trichloromethyl.

$R^{36}$ very particularly preferably represents hydrogen, fluorine, chlorine, bromine, iodine, methyl, trifluoromethyl, difluoromethyl or trichloromethyl.

$R^{36}$ especially preferably represents methyl.

$R^{37}$ and $R^{38}$ independently of one another preferably represent hydrogen, fluorine, chlorine, bromine, amino, nitro, methyl, ethyl or $C_1$-$C_2$-haloalkyl having 1 to 5 fluorine, chlorine and/or bromine atoms.

$R^{37}$ and $R^{38}$ independently of one another particularly preferably represent hydrogen, fluorine, chlorine, bromine, nitro, methyl, ethyl, trifluoromethyl, difluoromethyl, difluorochloromethyl or trichloromethyl.

$R^{37}$ and $R^{38}$ independently of one another very particularly preferably represent hydrogen, fluorine, chlorine, bromine, methyl, trifluoromethyl, difluoromethyl or trichloromethyl.

$R^{37}$ and $R^{38}$ especially preferably each represent hydrogen.

$R^{39}$ preferably represents hydrogen, fluorine, chlorine, bromine, methyl, ethyl or $C_1$-$C_2$-haloalkyl having 1 to 5 fluorine, chlorine and/or bromine atoms, $R^{39}$ particularly preferably represents hydrogen, fluorine, chlorine, bromine, methyl, ethyl, trifluoromethyl, difluoromethyl, difluorochloromethyl or trichloromethyl.

$R^{39}$ very particularly preferably represents hydrogen, fluorine, chlorine, bromine, methyl, trifluoromethyl, difluoromethyl or trichloromethyl.

$R^{39}$ especially preferably represents methyl.

$R^{40}$ preferably represents hydrogen, fluorine, chlorine, bromine, amino, $C_1$-$C_4$-alkylamino, di($C_1$-$C_4$-alkyl)amino, cyano, methyl, ethyl or $C_1$-$C_2$-haloalkyl having 1 to 5 fluorine, chlorine and/or bromine atoms.

$R^{40}$ particularly preferably represents hydrogen, fluorine, chlorine, bromine, amino, methylamino, dimethylamino, cyano, methyl, ethyl, trifluoromethyl, difluoromethyl, difluorochloromethyl or trichloromethyl.

$R^{40}$ very particularly preferably represents hydrogen, fluorine, chlorine, bromine, amino, methylamino, dimethylamino, methyl, trifluoromethyl, difluoromethyl or trichloromethyl.

$R^{40}$ especially preferably represents amino, methylamino, dimethylamino, methyl or trifluoromethyl.

$R^{41}$ preferably represents fluorine, chlorine, bromine, methyl, ethyl or $C_1$-$C_2$-haloalkyl having 1 to 5 fluorine, chlorine and/or bromine atoms.

$R^{41}$ particularly preferably represents fluorine, chlorine, bromine, methyl, ethyl, trifluoromethyl, difluoromethyl, difluorochloromethyl or trichloromethyl.

$R^{41}$ very particularly preferably represents fluorine, chlorine, bromine, methyl, trifluoromethyl, difluoromethyl or trichloromethyl.

$R^{41}$ especially preferably represents methyl, trifluoromethyl or difluoromethyl.

$R^{42}$ preferably represents hydrogen, fluorine, chlorine, bromine, amino, $C_1$-$C_4$-alkylamino, di($C_1$-$C_4$-alkyl)amino, cyano, methyl, ethyl or $C_1$-$C_2$-haloalkyl having 1 to 5 fluorine, chlorine and/or bromine atoms.

$R^{42}$ particularly preferably represents hydrogen, fluorine, chlorine, bromine, amino, methylamino, dimethylamino, cyano, methyl, ethyl, trifluoromethyl, difluoromethyl, difluorochloromethyl or trichloromethyl.

$R^{42}$ very particularly preferably represents hydrogen, fluorine, chlorine, bromine, amino, methylamino, dimethylamino, methyl, trifluoromethyl, difluoromethyl or trichloromethyl.

$R^{42}$ especially preferably represents amino, methylamino, dimethylamino, methyl or trifluoromethyl.

$R^{43}$ preferably represents fluorine, chlorine, bromine, methyl, ethyl or $C_1$-$C_2$-haloalkyl having 1 to 5 fluorine, chlorine and/or bromine atoms.

$R^{43}$ particularly preferably represents fluorine, chlorine, bromine, methyl, ethyl, trifluoromethyl, difluoromethyl, difluorochloromethyl or trichloromethyl.

$R^{43}$ very particularly preferably represents fluorine, chlorine, bromine, methyl, trifluoromethyl, difluoromethyl or trichloromethyl.

$R^{43}$ especially preferably represents methyl, trifluoromethyl or difluoromethyl.

$R^{44}$ preferably represents fluorine, chlorine, bromine, methyl, ethyl or $C_1$-$C_2$-haloalkyl having 1 to 5 fluorine, chlorine and/or bromine atoms.

$R^{44}$ particularly preferably represents fluorine, chlorine, bromine, methyl, ethyl, trifluoromethyl, difluoromethyl, difluorochloromethyl or trichloromethyl.

$R^{44}$ very particularly preferably represents fluorine, chlorine, bromine, methyl, trifluoromethyl, difluoromethyl or trichloromethyl.

$R^{45}$ preferably represents hydrogen, methyl or ethyl.

$R^{45}$ particularly preferably represents methyl.

$R^{46}$ preferably represents fluorine, chlorine, bromine, methyl or ethyl.

$R^{46}$ particularly preferably represents fluorine, chlorine or methyl.

$R^{47}$ preferably represents methyl, ethyl or $C_1$-$C_2$-haloalkyl having 1 to 5 fluorine, chlorine and/or bromine atoms.

$R^{47}$ particularly preferably represents methyl, ethyl, trifluoromethyl, difluoromethyl, difluorochloromethyl or trichloromethyl.

$R^{47}$ very particularly preferably represents methyl, trifluoromethyl, difluoromethyl or trichloromethyl.

$R^{47}$ especially preferably represents methyl or trifluoromethyl.

$R^{48}$ preferably represents hydrogen, fluorine, chlorine, bromine, methyl, ethyl or $C_1$-$C_2$-haloalkyl having 1 to 5 fluorine, chlorine and/or bromine atoms.

$R^{48}$ particularly preferably represents hydrogen, fluorine, chlorine, bromine, methyl or trifluoromethyl.

$R^{49}$ preferably represents fluorine, chlorine, bromine, iodine, hydroxyl, $C_1$-$C_4$-alkyl, methoxy, ethoxy, methylthio, ethylthio, difluoromethylthio, trifluoromethylthio, $C_1$-$C_2$-haloalkyl or $C_1$-$C_2$-haloalkoxy having in each case 1 to 5 fluorine, chlorine and/or bromine atoms.

$R^{49}$ particularly preferably represents fluorine, chlorine, bromine, iodine, methyl, ethyl, n-propyl, isopropyl, n-butyl, isobutyl, sec-butyl, tert-butyl, trifluoromethyl, difluoromethyl, difluorochloromethyl or trichloromethyl.

$R^{49}$ very particularly preferably represents fluorine, chlorine, bromine, iodine, methyl, trifluoromethyl, difluoromethyl or trichloromethyl.

$R^{50}$ preferably represents methyl, ethyl, n-propyl or isopropyl.

$R^{50}$ particularly preferably represents methyl or ethyl.

Preference is given to those compounds of the formula (I) in which all radicals each have the preferred meanings mentioned above.

Particular preference is given to those compounds of the formula (I) in which all radicals each have the particularly preferred meanings mentioned above.

Compounds of formula (II):

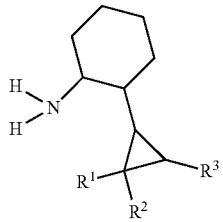

where $R^1$, $R^2$ and $R^3$ are defined above for a compound of formula (I), are also novel and are useful as intermediates in the preparation of compounds of formula (I).

The compounds of formula (I) may exist as different geometric or optical isomers or in different tautomeric forms. This invention covers all such isomers and tautomers and mixtures thereof in all proportions as well as isotopic forms such as deuterated compounds.

The compounds according to formula (I) may be prepared according to the following reaction scheme P0.

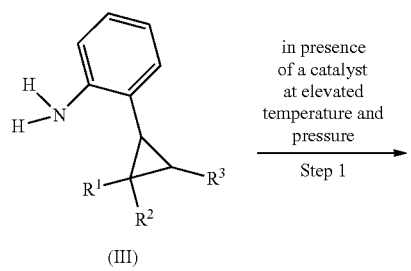

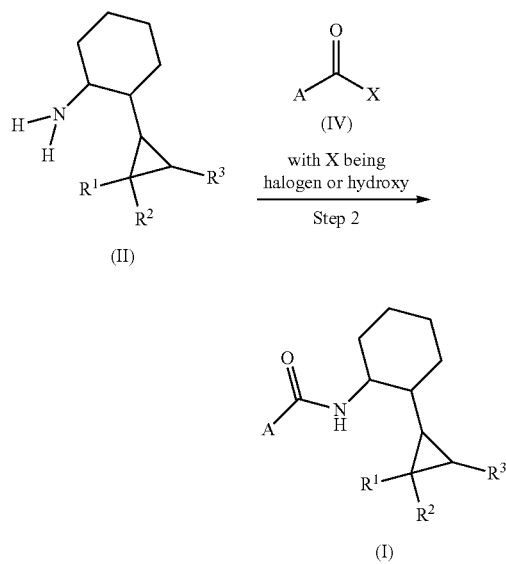

wherein $R^1$, $R^2$ and $R^3$ is defined as above.

The compounds according to formula (I) may be prepared according to the reaction scheme P0 wherein in step 1a a compound according to formula (III)

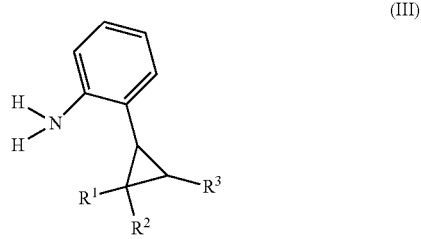

wherein $R^1$, $R^2$ and $R^3$ is as defined above;
are reacted in the presence of a catalyst at elevated temperature and pressure to obtain the compounds according to formula (II)

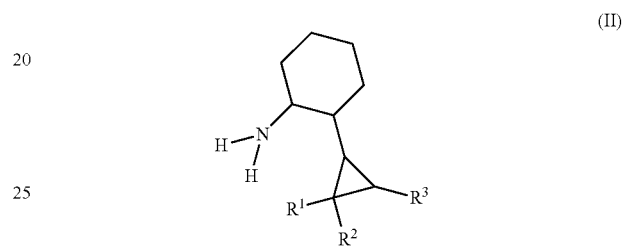

wherein $R^1$, $R^2$ and $R^3$ is as defined above;
wherein in step 2 the compounds according to formula (II) as defined in step 1 are reacted with compounds according to formula (IV)

with X being halogen or hydroxy;
to obtain the compounds according to formula (I)

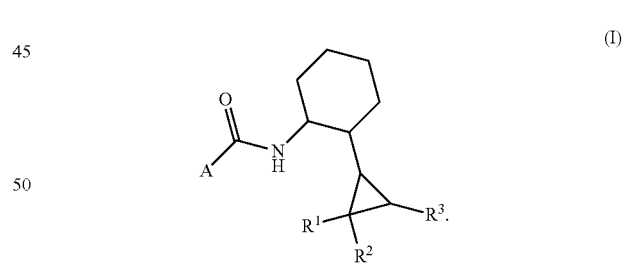

wherein A, $R^1$, $R^2$ and $R^3$ is as defined above;
Most materials, in particular heterocyclic acids and acid halides [that is, compounds of formula (IV)] are generally known from the literature, are commercially available or may be synthesized according to known methods (e.g. see WO-A 03/074491).

The compounds according to formula (III) are known from prior art as described in WO-A 2003/074491.

The compounds of formula (II) [where $R^1$ to $R^3$ is as defined above for a compound according to formula (I)] is obtained from a compound of formula (III) by catalytical reduction, e.g. Ru/C optionally in a solvent (such as methanol, ethanol or THF) at elevated temperature and pressure, to produce a crude isomere mixture of a compound of formula (II), which may be further purified by standard techniques.

A cis-/trans-mixture of a compound according to formula (II) may be extracted and subsequent separation of the cis- and trans-isomers achieved by using flash chromatography.

The reduction of step 1 is usually carried out at elevated temperatures of 0 to 200° C., preferably 0 to 120° C., more preferably of 50 to 120° C., and can be carried out at standard pressure or under excess pressure which means pressure up to 150 bar, preferably 1 to 150 bar, more preferably 5 to 120 bar, more preferably 10 to 100 bar. Additional ranges are 10 to 180° C., 20 to 150° C. and 50 to 150° C.

The reduction according to step 1 with the chlorinating agent is carried out neat or in the presence of a solvent which is inert under the prevailing reaction conditions. Use may be made, as diluents, for example, of mono or polychlorinated aliphatic or aromatic hydrocarbons or mixtures thereof. Examples of suitable diluents are chlorobenzene, dichlorobenzenes, trichlorobenzenes, chlorotoluenes, chlorobenzotrifluorides, methylene chloride, dichloroethane, chloroform or carbon tetrachloride. Preferred diluents are chlorobenzene, 1,2-dichlorobenzene, 1,3-dichlorobenzene, 1,4-dichlorobenzene, 1,2,3-trichlorobenzene, 1,2,4-trichlorobenzene, 4-chloro-trifluoromethylbenzene, 1,3,5-trichlorobenzene, 2 chlorotoluene, 3-chlorotoluene, 4-chlorotoluene or a mixture thereof. Use is particularly preferably made of chlorobenzene.

The reduction according to step 1 is carried out neat or in the presence of a suitable catalyst such a catalyst is Ru/C.

Surprisingly, it has now been found that the novel compounds of formula (I) have, for practical purposes, a very advantageous spectrum of activities for protecting plants against diseases that are caused by fungi as well as by bacteria and viruses.

The compounds of formula (I) can be used in the agricultural sector and related fields of use as active ingredients for controlling plant pests. The novel compounds are distinguished by excellent activity at low rates of application, by being well tolerated by plants and by being environmentally safe. They have very useful curative, preventive and systemic properties and are used for protecting numerous cultivated plants. The compounds of formula I can be used to inhibit or destroy the pests that occur on plants or parts of plants (fruit, blossoms, leaves, stems, tubers, roots) of different crops of useful plants, while at the same time protecting also those parts of the plants that grow later e.g. from phytopathogenic microorganisms.

It is also possible to use compounds of formula (I) as dressing agents for the treatment of plant propagation material, in particular of seeds (fruit, tubers, grains) and plant cuttings (e.g. rice), for the protection against fungal infections as well as against phytopathogenic fungi occurring in the soil.

Furthermore the compounds according to present invention may be used for controlling fungi in related areas, for example in the protection of technical materials, including wood and wood related technical products, in food storage, in hygiene management, etc.

The compounds of formula (I) are, for example, effective against the phytopathogenic fungi of the following classes:

Some pathogens of fungal diseases which can be treated according to the invention may be mentioned by way of example, but not by way of limitation:

Powdery Mildew Diseases such as *Blumeria* diseases caused for example by *Blumeria graminis*; *Podosphaera* diseases caused for example by *Podosphaera leucotricha*; *Sphaerotheca* diseases caused for example by *Sphaerotheca fuliginea*; *Uncinula* diseases caused for example by *Uncinula necator*;

Rust Diseases such as *Gymnosporangium* diseases caused for example by *Gymnosporangium sabinae*; *Hemileia* diseases caused for example by *Hemileia vastatrix*; *Phakopsora* diseases caused for example by *Phakopsora pachyrhizi* and *Phakopsora meibomiae*; *Puccinia* diseases caused for example by *Puccinia recondita*, *Puccinia graminis* or *Puccinia striiformis*; *Uromyces* diseases caused for example by *Uromyces appendiculatus*;

Oomycete Diseases such as *Albugo* diseases caused for example by *Albugo candida*; *Bremia* diseases caused for example by *Bremia lactucae*; *Peronospora* diseases caused for example by *Peronospora pisi* and *Peronospora brassicae*; *Phytophthora* diseases caused for example by *Phytophthora infestans*;

*Plasmopara* diseases caused for example by *Plasmopara viticola*; *Pseudoperonospora* diseases caused for example by *Pseudoperonospora humuli* and *Pseudoperonospora cubensis*; *Pythium* diseases caused for example by *Pythium ultimum*;

Leaf spot, Leaf blotch and Leaf Blight Diseases such as *Alternaria* diseases caused for example by *Alternaria solani*; *Cercospora* diseases caused for example by *Cercospora beticola*; *Cladiosporium* diseases caused for example by *Cladiosporium cucumerinum*; *Cochliobolus* diseases caused for example by *Cochliobolus sativus* (Conidiaform: *Drechslera*, Syn: *Helminthosporium*) or *Cochliobolus miyabeanus*; *Colletotrichum* diseases caused for example by *Colletotrichum lindemuthianum*; *Cycloconium* diseases caused for example by *Cycloconium oleaginum*; *Diaporthe* diseases caused for example by *Diaporthe citri*; *Elsinoe* diseases caused for example by *Elsinoe fawcettii*; *Gloeosporium* diseases caused for example by *Gloeosporium laeticolor*; *Glomerella* diseases caused for example by *Glomerella cingulata*; *Guignardia* diseases caused for example by *Guignardia bidwellii*; *Leptosphaeria* diseases caused for example by *Leptosphaeria maculans* and *Leptosphaeria nodorum*; *Magnaporthe* diseases caused for example by *Magnaporthe grisea*; *Mycosphaerella* diseases caused for example by *Mycosphaerella graminicola*, *Mycosphaerella arachidicola* and *Mycosphaerella fijiensis*; *Phaeosphaeria* diseases caused for example by *Phaeosphaeria nodorum*; *Pyrenophora* diseases caused for example by *Pyrenophora teres* or *Pyrenophora tritici repentis*; *Ramularia*-diseases caused for example by *Ramularia collocygni* or *Ramularia* areola; *Rhynchosporium* diseases caused for example by *Rhynchosporium secalis*; *Septoria* diseases caused for example by *Septoria apii* and *Septoria lycopersici*; *Typhula* diseases caused for example by *Thyphula incarnata*; *Venturia* diseases caused for example by *Venturia inaequalis*;

Root-, Sheath and Stem Diseases such as *Corticium* diseases caused for example by *Corticium graminearum*; *Fusarium* diseases caused for example by *Fusarium oxysporum*; *Gaeumannomyces* diseases caused for example by *Gaeumannomyces graminis*; *Rhizoctonia* diseases caused for example by *Rhizoctonia solani*; *Sarocladium* diseases caused for example by *Sarocladium oryzae*; *Sclerotium* diseases caused for example by *Sclerotium oryzae*; *Tapesia* diseases caused for example by *Tapesia acuformis*; *Thielaviopsis* diseases caused for example by *Thielaviopsis basicola*;

Ear and Panicle Diseases including Maize cob such as *Alternaria* diseases caused for example by *Alternaria* spp.; *Aspergillus* diseases caused for example by *Aspergillus flavus*; *Cladosporium* diseases caused for example by *Cladosporium cladosporioides*; *Claviceps* diseases caused for example by *Claviceps purpurea; Fusarium* diseases caused for example by *Fusarium culmorum; Gibberella* diseases caused for example by *Gibberella zeae; Monographella* diseases caused for example by *Monographella nivalis;*

Smut- and Bunt Diseases such as *Sphacelotheca* diseases caused for example by *Sphacelotheca reiliana; Tilletia* diseases caused for example by *Tilletia caries; Urocystis* diseases caused for example by *Urocystis occulta; Ustilago* diseases caused for example by *Ustilago nuda;*

Fruit Rot and Mould Diseases such as *Aspergillus* diseases caused for example by *Aspergillus flavus; Botrytis* diseases caused for example by *Botrytis cinerea; Penicillium* diseases caused for example by *Penicillium expansum* and *Penicillium purpurogenum; Rhizopus* diseases caused by example by *Rhizopus stolonifer Sclerotinia* diseases caused for example by *Sclerotinia sclerotiorum; Verticillium* diseases caused for example by *Verticillium alboatrum;*

Seed- and Soilborne Decay, Mould, Wilt, Rot and Damping-off diseases caused for example by *Alternaria* diseases caused for example by *Alternaria brassicicola; Aphanomyces* diseases caused for example by *Aphanomyces euteiches; Ascochyta* diseases caused for example by *Ascochyta lentis; Aspergillus* diseases caused for example by *Aspergillus flavus; Cladosporium* diseases caused for example by *Cladosporium herbarum; Cochliobolus* diseases caused for example by *Cochliobolus sativus;* (Conidiaform: *Drechslera, Bipolaris* Syn: *Helminthosporium*); *Colletotrichum* diseases caused for example by *Colletotrichum coccodes; Fusarium* diseases caused for example by *Fusarium culmorum; Gibberella* diseases caused for example by *Gibberella zeae; Macrophomina* diseases caused for example by *Macrophomina phaseolina; Microdochium* diseases caused for example by *Microdochium nivale; Monographella* diseases caused for example by *Monographella nivalis; Penicillium* diseases caused for example by *Penicillium expansum; Phoma* diseases caused for example by *Phoma lingam; Phomopsis* diseases caused for example by *Phomopsis sojae; Phytophthora* diseases caused for example by *Phytophthora cactorum; Pyrenophora* diseases caused for example by *Pyrenophora graminea; Pyricularia* diseases caused for example by *Pyricularia oryzae; Pythium* diseases caused for example by *Pythium ultimum; Rhizoctonia* diseases caused for example by *Rhizoctonia solani; Rhizopus* diseases caused for example by *Rhizopus oryzae; Sclerotium* diseases caused for example by *Sclerotium rolfsii; Septoria* diseases caused for example by *Septoria nodorum; Typhula* diseases caused for example by *Typhula incarnata; Verticillium* diseases caused for example by *Verticillium dahliae;*

Canker, Broom and Dieback Diseases such as *Nectria* diseases caused for example by *Nectria galligena;*

Blight Diseases such as *Monilinia* diseases caused for example by *Monilinia laxa;*

Leaf Blister or Leaf Curl Diseases including deformation of blooms and fruits such as *Exobasidium* diseases caused for example by *Exobasidium vexans.*

*Taphrina* diseases caused for example by *Taphrina deformans;*

Decline Diseases of Wooden Plants such as Esca disease caused for example by *Phaeomoniella clamydospora, Phaeoacremonium aleophilum* and *Fomitiporia mediterranea; Ganoderma* diseases caused for example by *Ganoderma boninense; Rigidoporus* diseases caused for example by *Rigidoporus lignosus*

Diseases of Flowers and Seeds such as *Botrytis* diseases caused for example by *Botrytis cinerea;*

Diseases of Tubers such as *Rhizoctonia* diseases caused for example by *Rhizoctonia solani;*

*Helminthosporium* diseases caused for example by *Helminthosporium solani;*

Club root diseases such as *Plasmodiophora* diseases, cause for example by *Plamodiophora brassicae.*

Diseases caused by Bacterial Organisms such as *Xanthomonas* species for example *Xanthomonas campestris* pv. *oryzae; Pseudomonas* species for example *Pseudomonas syringae* pv. *lachrymans; Erwinia* species for example *Erwinia amylovora.*

Fungal diseases on leaves, stems, pods and seeds caused, for example, by *alternaria* leaf spot (*Alternaria* spec. *atrans tenuissima*), anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera trispora* (Syn.)), dactuliophora leaf spot (*Dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllostica leaf spot (*Phyllosticta sojaecola*), pod and stem blight (*Phomopsis sojae*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi Phakopsora meibomiae*), scab (*Sphaceloma glycines*), stemphylium leaf blight (*Stemphylium botryosum*), target spot (*Corynespora cassiicola*).

Fungal diseases on roots and the stem base caused, for example, by black root rot (*Calonectria crotalariae*), charcoal rot (*Macrophomina phaseolina*), fusarium blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmopspora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidermatum, Pythium irregulare, Pythium debaryanum, Pythium myriotylum, Pythium ultimum*), rhizoctonia root rot, stem decay, and damping off (*Rhizoctonia solani*), sclerotinia stem decay (*Sclerotinia sclerotiorum*), sclerotinia Southern blight (*Sclerotinia rolfsii*), thielaviopsis root rot (*Thielaviopsis basicola*).

Furthermore, the novel compounds of formula I are effective against phytopathogenic bacteria and viruses (e.g. against *Xanthomonas* spp, *Pseudomonas* spp, *Erwinia amylovora* as well as against the tobacco mosaic virus).

It is also possible to control resistant strains of the organisms mentioned above.

Microorganisms capable of degrading or changing the industrial materials which may be mentioned are, for example, bacteria, fungi, yeasts, algae and slime organisms. The active compounds according to the invention preferably act against fungi, in particular moulds, wood-discolouring and wood-destroying fungi (Basidiomycetes) and against slime organisms and algae. Microorganisms of the following genera may be mentioned as examples: *Alternaria*, such as *Alternaria tenuis, Aspergillus*, such as *Aspergillus niger, Chaetomium*, such as *Chaetomium globosum, Coniophora*, such as *Coniophora puetana, Lentinus*, such as *Lentinus tigrinus, Penicillium*, such as *Penicillium glaucum, Polyporus*, such as *Polyporus versicolor, Aureobasidium*, such as *Aureobasidium pullulans, Sclerophoma*, such as *Sclerophoma pityophila, Trichoderma*, such as *Trichoderma viride,*

*Escherichia*, such as *Escherichia coli*, *Pseudomonas*, such as *Pseudomonas aeruginosa*, and *Staphylococcus*, such as *Staphylococcus aureus*.

The application of the compositions according to the invention on growing plants or plant parts, they can also be used to protect plants or plant parts after harvesting.

Within this application "post-harvest treatment" is to be understood in a very broad sense. On the one hand it means literally the treatment of fruit or vegetables after the fruit and vegetables have been harvested. For post-harvest treatment the fruit or vegetable is treated with (e.g. with using the method and apparatus disclosed in WO 2005/009474), dipped or tank dumped or drenched into a liquid, brushed with, fumigated, painted, fogged (warm or cold), or the fruit may be coated with a waxy or other composition. It is also possible to protect plants or plant parts against post-harvest and storage diseases by applying the compositions according to the invention shortly before the harvest, while their efficacy persists during transport and storage.

According to the invention, post-harvest and storage diseases may be caused for example by the following fungi: *Colletotrichum* spp., e.g. *Colletotrichum musae*, *Colletotrichum gloeosporioides*, *Colletotrichum coccodes*; *Fusarium* spp., e.g. *Fusarium semitectum*, *Fusarium moniliforme*, *Fusarium solani*, *Fusarium oxysporum*; *Verticillium* spp., e.g. *Verticillium theobromae*; *Nigrospora* spp.; *Botrytis* spp., e.g. *Botrytis cinerea*; *Geotrichum* spp., e.g. *Geotrichum candidum*; *Phomopsis* spp., *Phomopsis natalensis*; *Diplodia* spp., e.g. *Diplodia citri*; *Alternaria* spp., e.g. *Alternaria citri*, *Alternaria alternata*; *Phytophthora* spp., e.g. *Phytophthora citrophthora*, *Phytophthora fragariae*, *Phytophthora cactorum*, *Phytophthora parasitica*; *Septoria* spp., e.g. *Septoria depressa*; *Mucor* spp., e.g. *Mucor piriformis*; *Monilinia* spp., e.g. *Monilinia fructigena*, *Monilinia laxa*; *Venturia* spp., e.g. *Venturia inaequalis*, *Venturia pyrina*; *Rhizopus* spp., e.g. *Rhizopus stolonifer*, *Rhizopus oryzae*; *Glomerella* spp., e.g. *Glomerella cingulata*; *Sclerotinia* spp., e.g. *Sclerotinia fruiticola*; *Ceratocystis* spp., e.g. *Ceratocystis paradoxa*; *Penicillium* spp., e.g. *Penicillium funiculosum*, *Penicillium expansum*, *Penicillium digitatum*, *Penicillium italicum*; *Gloeosporium* spp., e.g. *Gloeosporium album*, *Gloeosporium perennans*, *Gloeosporium fructigenum*, *Gloeosporium singulata*; *Phlyctaena* spp., e.g. *Phlyctaena vagabunda*; *Cylindrocarpon* spp., e.g. *Cylindrocarpon mali*; *Stemphyllium* spp., e.g. *Stemphyllium vesicarium*; *Phacydiopycnis* spp., e.g. *Phacydiopycnis malirum*; *Thielaviopsis* spp., e.g. *Thielaviopsis paradoxy*; *Aspergillus* spp., e.g. *Aspergillus niger*, *Aspergillus carbonarius*; *Nectria* spp., e.g. *Nectria galligena*; *Pezicula* spp.

According to the invention, post-harvest storage disorders are for example scald, scorch, softening, senescent breakdown, lenticel spots, bitter pit, browning, water core, vascular breakdown, $CO_2$ injury, $CO_2$ deficiency and $O_2$ deficiency.

Fruit, cutflower and vegetables to be treated according to the invention are particularly selected from cereals, e.g. wheat, barley, rye, oats, rice, sorghum and the like; beets, e.g. sugar beet and fodder beet; pome and stone fruit and berries, e.g. apples, pears, plums, peaches, almonds, cherries, strawberries, raspberries and blackberries; leguminous plants, e.g. beans, lentils, peas, soy beans; oleaginous plants, e.g. rape, mustard, poppy, olive, sunflower, coconut, castor-oil plant, cocoa, ground-nuts; *cucurbitaceae*, e.g. pumpkins, gherkins, melons, cucumbers, squashes; fibrous plants, e.g. cotton, flax, hemp, jute; citrus fruit, e.g. orange, lemon, grapefruit, mandarin; tropical fruit, e.g. papaya, passion fruit, mango, carambola, pineapple, banana; vegetables, e.g. spinach, lettuce, asparagus, brassicaceae such as cabbages and turnips, carrots, onions, tomatoes, potatoes, hot and sweet peppers; laurel-like plants, e.g. avocado, cinnamon, camphor tree; or plants such as maize, tobacco, nuts, coffee, sugar-cane, tea, grapevines, hops, rubber plants, as well as ornamental plants, e.g. cutflowers, roses, gerbera and flower bulbs, shrubs, deciduous trees and evergreen trees such as conifers. This enumeration of culture plants is given with the purpose of illustrating the invention and not to delimiting it thereto.

According to the invention all plants and plant parts can be treated. By plants is meant all plants and plant populations such as desirable and undesirable wild plants, cultivars and plant varieties (whether or not protectable by plant variety or plant breeder's rights). Cultivars and plant varieties can be plants obtained by conventional propagation and breeding methods which can be assisted or supplemented by one or more biotechnological methods such as by use of double haploids, protoplast fusion, random and directed mutagenesis, molecular or genetic markers or by bioengineering and genetic engineering methods. By plant parts is meant all above ground and below ground parts and organs of plants such as shoot, leaf, blossom and root, whereby for example leaves, needles, stems, branches, blossoms, fruiting bodies, fruits and seed as well as roots, tubers, corms and rhizomes are listed. Crops and vegetative and generative propagating material, for example cuttings, corms, rhizomes, tubers, runners and seeds also belong to plant parts.

Among the plants that can be protected by the method according to the invention, mention may be made of major field crops like corn, soybean, cotton, *Brassica* oilseeds such as *Brassica napus* (e.g. canola), *Brassica rapa*, *B. juncea* (e.g. mustard) and *Brassica carinata*, rice, wheat, sugarbeet, sugarcane, oats, rye, barley, millet, triticale, flax, vine and various fruits and vegetables of various botanical taxa such as *Rosaceae* sp. (for instance pip fruit such as apples and pears, but also stone fruit such as apricots, cherries, almonds and peaches, berry fruits such as strawberries), *Ribesioidae* sp., *Juglandaceae* sp., *Betulaceae* sp., *Anacardiaceae* sp., *Fagaceae* sp., *Moraceae* sp., *Oleaceae* sp., *Actimidaceae* sp., *Lauraceae* sp., *Musaceae* sp. (for instance banana trees and plantings), *Rubiaceae* sp. (for instance coffee), *Theaceae* sp., *Sterculiceae* sp., *Rutaceae* sp. (for instance lemons, oranges and grapefruit); *Solanaceae* sp. (for instance tomatoes, potatoes, peppers, eggplant), *Liliaceae* sp., *Compositiae* sp. (for instance lettuce, artichoke and chicory—including root chicory, endive or common chicory), *Umbelliferae* sp. (for instance carrot, parsley, celery and celeriac), *Cucurbitaceae* sp. (for instance cucumber—including pickling cucumber, squash, watermelon, gourds and melons), *Alliaceae* sp. (for instance onions and leek), *Cruciferae* sp. (for instance white cabbage, red cabbage, broccoli, cauliflower, brussel sprouts, pak choi, kohlrabi, radish, horseradish, cress, Chinese cabbage), *Leguminosae* sp. (for instance peanuts, peas and beans beans—such as climbing beans and broad beans), *Chenopodiaceae* sp. (for instance mangold, spinach beet, spinach, beetroots), *Malvaceae* (for instance okra), *Asparagaceae* (for instance asparagus); horticultural and forest crops; ornamental plants; as well as genetically modified homologues of these crops.

The method of treatment according to the invention can be used in the treatment of genetically modified organisms (GMOs), e.g. plants or seeds. Genetically modified plants (or transgenic plants) are plants of which a heterologous gene has been stably integrated into genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example, antisense technology, cosuppression technology or RNA interference—RNAi—technology). A heterologous gene that is located in the genome is also called a transgene. A transgene that is defined by its particular location in the plant genome is called a transformation or transgenic event.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the active compounds and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf color, earlier flowering, higher quality and/or a higher nutritional value of the harvested products, higher sugar concentration within the fruits, better storage stability and/or processability of the harvested products are possible, which exceed the effects which were actually to be expected.

At certain application rates, the active compound combinations according to the invention may also have a strengthening effect in plants. Accordingly, they are also suitable for mobilizing the defense system of the plant against attack by unwanted microorganisms. This may, if appropriate, be one of the reasons of the enhanced activity of the combinations according to the invention, for example against fungi. Plant-strengthening (resistance-inducing) substances are to be understood as meaning, in the present context, those substances or combinations of substances which are capable of stimulating the defense system of plants in such a way that, when subsequently inoculated with unwanted microorganisms, the treated plants display a substantial degree of resistance to these microorganisms. In the present case, unwanted microorganisms are to be understood as meaning phytopathogenic fungi, bacteria and viruses. Thus, the substances according to the invention can be employed for protecting plants against attack by the abovementioned pathogens within a certain period of time after the treatment. The period of time within which protection is effected generally extends from 1 to 10 days, preferably 1 to 7 days, after the treatment of the plants with the active compounds.

Plants and plant cultivars which are preferably to be treated according to the invention include all plants which have genetic material which impart particularly advantageous, useful traits to these plants (whether obtained by breeding and/or biotechnological means).

Plants and plant cultivars which are also preferably to be treated according to the invention are resistant against one or more biotic stresses, i.e. said plants show a better defense against animal and microbial pests, such as against nematodes, insects, mites, phytopathogenic fungi, bacteria, viruses and/or viroids.

Examples of nematode resistant plants are described in e.g. U.S. patent application Ser. Nos. 11/765,491, 11/765,494, 10/926,819, 10/782,020, 12/032,479, 10/783,417, 10/782,096, 11/657,964, 12/192,904, 11/396,808, 12/166,253, 12/166,239, 12/166,124, 12/166,209, 11/762,886, 12/364,335, 11/763,947, 12/252,453, 12/209,354, 12/491,396 and 12/497,221.

Plants and plant cultivars which may also be treated according to the invention are those plants which are resistant to one or more abiotic stresses. Abiotic stress conditions may include, for example, drought, cold temperature exposure, heat exposure, osmotic stress, flooding, increased soil salinity, increased mineral exposure, ozone exposure, high light exposure, limited availability of nitrogen nutrients, limited availability of phosphorus nutrients, shade avoidance.

Plants and plant cultivars which may also be treated according to the invention, are those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated according to the invention are hybrid plants that already express the characteristic of heterosis or hybrid vigor which results in generally higher yield, vigor, health and resistance towards biotic and abiotic stresses). Such plants are typically made by crossing an inbred male-sterile parent line (the female parent) with another inbred male-fertile parent line (the male parent). Hybrid seed is typically harvested from the male sterile plants and sold to growers. Male sterile plants can sometimes (e.g. in corn) be produced by detasseling, i.e. the mechanical removal of the male reproductive organs (or males flowers) but, more typically, male sterility is the result of genetic determinants in the plant genome. In that case, and especially when seed is the desired product to be harvested from the hybrid plants it is typically useful to ensure that male fertility in the hybrid plants is fully restored. This can be accomplished by ensuring that the male parents have appropriate fertility restorer genes which are capable of restoring the male fertility in hybrid plants that contain the genetic determinants responsible for male-sterility. Genetic determinants for male sterility may be located in the cytoplasm. Examples of cytoplasmic male sterility (CMS) were for instance described in *Brassica* species. However, genetic determinants for male sterility can also be located in the nuclear genome. Male sterile plants can also be obtained by plant biotechnology methods such as genetic engineering. A particularly useful means of obtaining male-sterile plants is described in WO 89/10396 in which, for example, a ribonuclease such as barnase is selectively expressed in the tapetum cells in the stamens. Fertility can then be restored by expression in the tapetum cells of a ribonuclease inhibitor such as barstar.

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-resistant plants are for example glyphosate-tolerant plants, i.e. plants made tolerant to the herbicide glyphosate or salts thereof. Plants can be made tolerant to glyphosate through different means. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium* (Comai et al., 1983, Science 221, 370-371), the CP4 gene of the bacterium *Agrobacterium* sp. (Barry et al., 1992, Curr. Topics Plant Physiol. 7, 139-145), the genes encoding a Petunia EPSPS (Shah et al., 1986, Science 233, 478-481), a Tomato EPSPS (Gasser et al., 1988, J. Biol. Chem. 263, 4280-4289), or an Eleusine EPSPS (WO 01/66704). It can also be a mutated EPSPS. Glyphosate-tolerant plants can also be obtained by expressing a gene that encodes a glyphosate oxido-reductase enzyme. Glyphosate-tolerant plants can also be obtained by expressing a gene that encodes a glyphosate acetyl transferase enzyme. Glyphosate-tolerant plants can also be obtained by selecting plants containing naturally-occurring mutations of the above-mentioned genes. Plants expressing EPSPS genes that confer glyphosate tolerance are described. Plants comprising other genes that confer glyphosate tolerance, such as decarboxylase genes, are described.

Other herbicide resistant plants are for example plants that are made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. One such efficient detoxifying enzyme is an enzyme encoding a phosphinothricin acetyltransferase (such as the bar or pat protein from *Streptomyces* species). Plants expressing an exogenous phosphinothricin acetyltransferase are described.

Further herbicide-tolerant plants are also plants that are made tolerant to the herbicides inhibiting the enzyme hydroxyphenylpyruvatedioxygenase (HPPD). Hydroxyphenylpyruvatedioxygenases HPPD is an are enzyme that catalyze the reaction in which para-hydroxyphenylpyruvate (HPP) is transformed into homogentisate. Plants tolerant to HPPD-inhibitors can be transformed with a gene encoding a naturally-occurring resistant HPPD enzyme, or a gene encoding a mutated or chimeric HPPD enzyme as described in WO 96/38567, WO 99/24585, and WO 99/24586, WO 2009/144079, WO 2002/046387, or U.S. Pat. No. 6,768,044. Tolerance to HPPD-inhibitors can also be obtained by transforming plants with genes encoding certain enzymes enabling the formation of homogentisate despite the inhibition of the native HPPD enzyme by the HPPD-inhibitor. Such plants and genes are described in WO 99/34008 and WO 02/36787. Tolerance of plants to HPPD inhibitors can also be improved by transforming plants with a gene encoding an enzyme having prephenate deshydrogenase (PDH) activity in addition to a gene encoding an HPPD-tolerant enzyme, as described in WO 2004/024928. Further, plants can be made more tolerant to HPPD-inhibitor herbicides by adding into their genome a gene encoding an enzyme capable of metabolizing or degrading HPPD inhibitors, such as the CYP450 enzymes shown in WO 2007/103567 and WO 2008/150473.

Still further herbicide resistant plants are plants that are made tolerant to acetolactate synthase (ALS) inhibitors. Known ALS-inhibitors include, for example, sulfonylurea, imidazolinone, triazolopyrimidines, pryimidinyoxy(thio) benzoates, and/or sulfonylaminocarbonyltriazolinone herbicides. Different mutations in the ALS enzyme (also known as acetohydroxyacid synthase, AHAS) are known to confer tolerance to different herbicides and groups of herbicides, as described for example in Tranel and Wright (2002, Weed Science 50:700-712). The production of sulfonylurea-tolerant plants and imidazolinone-tolerant plants is described. Other imidazolinone-tolerant plants are also described. Further sulfonylurea- and imidazolinone-tolerant plants are also described.

Other plants tolerant to imidazolinone and/or sulfonylurea can be obtained by induced mutagenesis, selection in cell cultures in the presence of the herbicide or mutation breeding as described for example for soybeans in U.S. Pat. No. 5,084,082, for rice in WO 97/41218, for sugar beet in U.S. Pat. No. 5,773,702 and WO 99/057965, for lettuce in U.S. Pat. No. 5,198,599, or for sunflower in WO 01/065922.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

An "insect-resistant transgenic plant", as used herein, includes any plant containing at least one transgene comprising a coding sequence encoding:

1) an insecticidal crystal protein from *Bacillus thuringiensis* or an insecticidal portion thereof, such as the insecticidal crystal proteins listed by Crickmore et al. (1998, Microbiology and Molecular Biology Reviews, 62: 807-813), updated by Crickmore et al. (2005) at the *Bacillus thuringiensis* toxin nomenclature, online at: http://www.lifesci.sussex.ac.uk/Home/Neil_Crickmore/Bt/), or insecticidal portions thereof, e.g., proteins of the Cry protein classes Cry1Ab, Cry1Ac, Cry1B, Cry1C, Cry1D, Cry1F, Cry2Ab, Cry3Aa, or Cry3Bb or insecticidal portions thereof (e.g. EP 1999141 and WO 2007/107302), or such proteins encoded by synthetic genes as e.g. described in U.S. patent application Ser. No. 12/249,016; or 2) a crystal protein from *Bacillus thuringiensis* or a portion thereof which is insecticidal in the presence of a second other crystal protein from *Bacillus thuringiensis* or a portion thereof, such as the binary toxin made up of the Cry34 and Cry35 crystal proteins (Moellenbeck et al. 2001, Nat. Biotechnol. 19: 668-72; Schnepf et al. 2006, Applied Environm. Microbiol. 71, 1765-1774) or the binary toxin made up of the Cry1A or Cry1F proteins and the Cry2Aa or Cry2Ab or Cry2Ae proteins (U.S. patent application Ser. No. 12/214,022 and EP 08010791.5); or 3) a hybrid insecticidal protein comprising parts of different insecticidal crystal proteins from *Bacillus thuringiensis*, such as a hybrid of the proteins of 1) above or a hybrid of the proteins of 2) above, e.g., the Cry1A.105 protein produced by corn event MON89034 (WO 2007/027777); or 4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation, such as the Cry3Bb1 protein in corn events MON863 or MON88017, or the Cry3A protein in corn event MIR604; or 5) an insecticidal secreted protein from *Bacillus thuringiensis* or *Bacillus cereus*, or an insecticidal portion thereof, such as the vegetative insecticidal (VIP) proteins listed at: http://www.lifesci.sussex.ac.uk/home/Neil_Crickmore/Bt/vip.html, e.g., proteins from the VIP3Aa protein class; or 6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins (WO 94/21795); or 7) a hybrid insecticidal protein comprising parts from different secreted proteins from *Bacillus thuringiensis* or *Bacillus cereus*, such as a hybrid of the proteins in 1) above or a hybrid of the proteins in 2) above; or 8) a protein of any one of 5) to 7) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein), such as the VIP3Aa protein in cotton event COT102; or 9) a secreted protein from *Bacillus thuringiensis* or *Bacillus cereus* which is insecticidal in the presence of a crystal protein from *Bacillus thuringiensis*, such as the binary toxin made up of VIP3 and Cry1A or Cry1F (U.S. Patent Appl. Nos. 61/126,083 and 61/195,019), or the binary toxin made up of the VIP3 protein and the Cry2Aa or Cry2Ab or Cry2Ae proteins (U.S. patent application Ser. No. 12/214,022 and EP 08010791.5).

10) a protein of 9) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein)

Of course, an insect-resistant transgenic plant, as used herein, also includes any plant comprising a combination of genes encoding the proteins of any one of the above classes 1 to 10. In one embodiment, an insect-resistant plant contains more than one transgene encoding a protein of any one of the above classes 1 to 10, to expand the range of target insect species affected when using different proteins directed at different target insect species, or to delay insect resistance development to the plants by using different proteins insecticidal to the same target insect species but having a different mode of action, such as binding to different receptor binding sites in the insect.

An "insect-resistant transgenic plant", as used herein, further includes any plant containing at least one transgene comprising a sequence producing upon expression a double-stranded RNA which upon ingestion by a plant insect pest inhibits the growth of this insect pest.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance. Particularly useful stress tolerance plants include:

1) plants which contain a transgene capable of reducing the expression and/or the activity of poly(ADP-ribose) polymerase (PARP) gene in the plant cells or plants.

2) plants which contain a stress tolerance enhancing transgene capable of reducing the expression and/or the activity of the PARG encoding genes of the plants or plants cells.

3) plants which contain a stress tolerance enhancing transgene coding for a plant-functional enzyme of the nicotineamide adenine dinucleotide salvage synthesis pathway including nicotinamidase, nicotinate phosphoribosyltransferase, nicotinic acid mononucleotide adenyl transferase, nicotinamide adenine dinucleotide synthetase or nicotine amide phosphorybosyltransferase.

Plants or plant cultivars (obtained by plant biotechnology methods such as genetic engineering) which may also be treated according to the invention show altered quantity, quality and/or storage-stability of the harvested product and/or altered properties of specific ingredients of the harvested product such as:

1) transgenic plants which synthesize a modified starch, which in its physical-chemical characteristics, in particular the amylose content or the amylose/amylopectin ratio, the degree of branching, the average chain length, the side chain distribution, the viscosity behaviour, the gelling strength, the starch grain size and/or the starch grain morphology, is changed in comparison with the synthesised starch in wild type plant cells or plants, so that this is better suited for special applications.

2) transgenic plants which synthesize non starch carbohydrate polymers or which synthesize non starch carbohydrate polymers with altered properties in comparison to wild type plants without genetic modification. Examples are plants producing polyfructose, especially of the inulin and levan-type, plants producing alpha-1,4-glucans, plants producing alpha-1,6 branched alpha-1,4-glucans, plants producing alternan, 3) transgenic plants which produce hyaluronan.

4) transgenic plants or hybrid plants, such as onions with characteristics such as 'high soluble solids content', 'low pungency' (LP) and/or 'long storage' (LS).

Plants or plant cultivars (that can be obtained by plant biotechnology methods such as genetic engineering) which may also be treated according to the invention are plants, such as cotton plants, with altered fiber characteristics. Such plants can be obtained by genetic transformation, or by selection of plants contain a mutation imparting such altered fiber characteristics and include:

a) Plants, such as cotton plants, containing an altered form of cellulose synthase genes
b) Plants, such as cotton plants, containing an altered form of rsw2 or rsw3 homologous nucleic acids Plants, such as cotton plants, with increased expression of sucrose phosphate synthase
c) Plants, such as cotton plants, with increased expression of sucrose Plants, such as cotton plants, wherein the timing of the plasmodesmatal gating at the basis of the fiber cell is altered, e.g. through downregulation of fiber-selective β-1,3-glucanase
d) Plants, such as cotton plants, having fibers with altered reactivity, e.g. through the expression of N-acetylglucosaminetransferase gene including nodC and chitin synthase genes Plants or plant cultivars (that can be obtained by plant biotechnology methods such as genetic engineering) which may also be treated according to the invention are plants, such as oilseed rape or related *Brassica* plants, with altered oil profile characteristics. Such plants can be obtained by genetic transformation, or by selection of plants contain a mutation imparting such altered oil profile characteristics and include:

a) Plants, such as oilseed rape plants, producing oil having a high oleic acid content
b) Plants such as oilseed rape plants, producing oil having a low linolenic acid content
c) Plant such as oilseed rape plants, producing oil having a low level of saturated fatty acids Plants or plant cultivars (that can be obtained by plant biotechnology methods such as genetic engineering) which may also be treated according to the invention are plants, such as potatoes which are virus-resistant, e.g. against potato virus Y (event SY230 and SY233 from Tecnoplant, Argentina), which are disease resistant, e.g. against potato late blight (e.g. RB gene), which show a reduction in cold-induced sweetening (carrying the Nt-Inhh, IIR-INV gene) or which possess a dwarf phenotype (Gene A-20 oxidase).

Plants or plant cultivars (that can be obtained by plant biotechnology methods such as genetic engineering) which may also be treated according to the invention are plants, such as oilseed rape or related *Brassica* plants, with altered seed shattering characteristics. Such plants can be obtained by genetic transformation, or by selection of plants contain a mutation imparting such altered seed shattering characteristics and include plants such as oilseed rape plants with delayed or reduced seed shattering.

Particularly useful transgenic plants which may be treated according to the invention are plants containing transformation events, or combination of transformation events, that are the subject of petitions for non-regulated status, in the United States of America, to the Animal and Plant Health Inspection Service (APHIS) of the United States Department of Agriculture (USDA) whether such petitions are granted or are still pending. At any time this information is readily available from APHIS (4700 River Road Riverdale, Md. 20737, USA), for instance on its internet site (URL http://www.aphis.usda.gov/brs/not_reg.html). On the filing date of this application the petitions for nonregulated status that were pending with APHIS or granted by APHIS were those listed in table B which contains the following information:

Petition: the identification number of the petition. Technical descriptions of the transformation events can be found in the individual petition documents which are obtainable from APHIS, for example on the APHIS website, by reference to this petition number. These descriptions are herein incorporated by reference.

Extension of Petition: reference to a previous petition for which an extension is requested.

Institution: the name of the entity submitting the petition.

Regulated article: the plant species concerned.

Transgenic phenotype: the trait conferred to the plants by the transformation event.

Transformation event or line: the name of the event or events (sometimes also designated as lines or lines) for which nonregulated status is requested.

APHIS documents: various documents published by APHIS in relation to the Petition and which can be requested with APHIS.

Additional particularly useful plants containing single transformation events or combinations of transformation events are listed for example in the databases from various national or regional regulatory agencies (see for example http://gmoinfo.jrc.it/gmp_browse.aspx and http://cera-gmc.org/index.php?evidcode=&hstIDXCode=&gType=&AbbrCode=&atCode=&stCode=&coIDCode=&action=gm_crop_database&mode=Submit).

The compounds of formula (I) are used in unmodified form or, preferably, together with the adjuvants conventionally employed in the art of formulation. To this end they are conveniently formulated in known manner to emulsifiable concentrates, coatable pastes, directly sprayable or dilutable solutions, dilute emulsions, wettable powders, soluble powders, dusts, granulates, and also encapsulations e.g. in polymeric substances.

As with the type of the compositions, the methods of application, such as spraying, atomising, dusting, scattering, coating or pouring, are chosen in accordance with the intended objectives and the prevailing circumstances. The compositions may also contain further adjuvants such as stabilizers, antifoams, viscosity regulators, binders or tackifiers as well as fertilizers, micronutrient donors or other formulations for obtaining special effects.

Suitable carriers and adjuvants can be solid or liquid and are substances useful in formulation technology, e.g. natural or regenerated mineral substances, solvents, dispersants, wetting agents, tackifiers, thickeners, binders or fertilizers. Such carriers are for example described in WO 97/33890.

The compounds of formula (I) are normally used in the form of compositions and can be applied to the crop area or plant to be treated, simultaneously or in succession with further compounds. These further compounds can be e.g. fertilizers or micronutrient donors or other preparations which influence the growth of plants. They can also be selective herbicides as well as insecticides, fungicides, bactericides, nematicides, molluscicides or mixtures of several of these preparations, if desired together with further carriers, surfactants or application promoting adjuvants customarily employed in the art of formulation.

The compounds of formula (I) can be mixed with other fungicides, resulting in some cases in unexpected synergistic activities. Mixing components which are particularly preferred are azoles, such as azaconazole, BAY 14120, bitertanol, bromuconazole, cyproconazole, difenoconazole, diniconazole, epoxiconazole, fenbuconazole, fluquinconazole, flusilazole, flutriafol, hexaconazole, imazalil, imibenconazole, ipconazole, metconazole, myclobutanil, pefurazoate, penconazole, pyrifenox, prochloraz, propiconazole, simeconazole, tebuconazole, tetraconazole, triadimefon, triadimenol, triflumizole, triticonazole; pyrimidinyl carbinole, such as ancymidol, fenarimol, nuarimol; 2-amino-pyrimidines, such as bupirimate, dimethirimol, ethirimol; morpholines, such as dodemorph, fenpropidine, fenpropimorph, spiroxamine, tridemorph; anilinopyrimidines, such as cyprodinil, mepanipyrim, pyrimethanil; pyrroles, such as fenpiclonil, fludioxonil; phenylamides, such as benalaxyl, furalaxyl, metalaxyl, R-metalaxyl, ofurace, oxadixyl; benzimidazoles, such as benomyl, carbendazim, debacarb, fuberidazole, thiabendazole; dicarboximides, such as chlozolinate, dichlozoline, iprodione, myclozoline, procymidone, vinclozoline; carboxamides, such as carboxin, fenfuram, flutolanil, mepronil, oxycarboxin, thifluzamide; guanidines, such as guazatine, dodine, iminoctadine; strobilurines, such as azoxystrobin, kresoximmethyl, metominostrobin, SSF-129, trifloxystrobin, picoxystrobin, BAS 500F (proposed name pyraclostrobin), BAS 520; dithiocarbamates, such as ferbam, mancozeb, maneb, metiram, propineb, thiram, zineb, ziram; N-halomethylthiotetrahydrophthalimides, such as captafol, captan, dichlofluanid, fluoromides, folpet, tolyfluanid; Cu-compounds, such as Bordeaux mixture, copper hydroxide, copper oxychloride, copper sulfate, cuprous oxide, mancopper, oxine-copper; nitrophenol-derivatives, such as dinocap, nitrothal-isopropyl; organo-p-derivatives, such as edifenphos, iprobenphos, isoprothiolane, phosdiphen, pyrazophos, tolclofos-methyl; various others, such as acibenzolar-5-methyl, anilazine, benthiavalicarb, blasticidin-S, chinomethionate, chloroneb, chlorothalonil, cyflufenamid, cymoxanil, dichlone, diclomezine, dicloran, diethofencarb, dimethomorph, SYP-LI90 (proposed name: flumorph), dithianon, ethaboxam, etridiazole, famoxadone, fenamidone, fenoxanil, fentin, ferimzone, fluazinam, flusulfamide, fenhexamid, fosetyl-aluminium, hymexazol, iprovalicarb, IKF-916 (cyazofamid), kasugamycin, methasulfocarb, metrafenone, nicobifen, pencycuron, phthalide, polyoxins, probenazole, propamocarb, pyroquilon, quinoxyfen, quintozene, sulfur, triazoxide, tricyclazole, triforine, validamycin, zoxamide (RH7281).

A preferred method of applying a compound of formula (I), or an agrochemical composition which contains at least one of said compounds, is foliar application. The frequency of application and the rate of application will depend on the risk of infestation by the corresponding pathogen. However, the compounds of formula I can also penetrate the plant through the roots via the soil (systemic action) by drenching the locus of the plant with a liquid formulation, or by applying the compounds in solid form to the soil, e.g. in granular form (soil application). In crops of water rice such granulates can be applied to the flooded rice field. The compounds of formula I may also be applied to seeds (coating) by impregnating the seeds or tubers either with a liquid formulation of the fungicide or coating them with a solid formulation.

A formulation [that is, a composition containing the compound of formula (I)] and, if desired, a solid or liquid adjuvant, is prepared in a known manner, typically by intimately mixing and/or grinding the compound with extenders, for example solvents, solid carriers and, optionally, surface active compounds (surfactants).

The agrochemical formulations will usually contain from 0.1 to 99% by weight, preferably from 0.1 to 95% by weight, of the compound of formula I, 99.9 to 1% by weight, preferably 99.8 to 5% by weight, of a solid or liquid adjuvant, and from 0 to 25% by weight, preferably from 0.1 to 25% by weight, of a surfactant.

Advantageous rates of application are normally from 5 g to 2 kg of active ingredient (a. i.) per hectare (ha), preferably from 10 g to 1 kg a. i./ha, most preferably from 20 g to 600 g a. i./ha. When used as seed drenching agent, convenient dosages are from 10 mg to 1 g of active substance per kg of seeds.

Whereas it is preferred to formulate commercial products as concentrates, the end user will normally use dilute formulations.

The following non-limiting Examples illustrate the above-described invention in more detail.

Most materials heterocyclic acids and acid halides (compounds according to formula (IV) as described above are generally known from the literature (WO-A 2003/074491 and references cited therein) or may be synthesized according to known methods.

The present invention also relates to a process for the preparation of specific difluoromethylpyrazol derivatives according to formula (IVc) and (IVf). Thus according to a further aspect of the present invention there is provided a process P1 for the preparation of compounds of formula (IVc) and (IVf) as illustrated by the following reaction scheme P1:

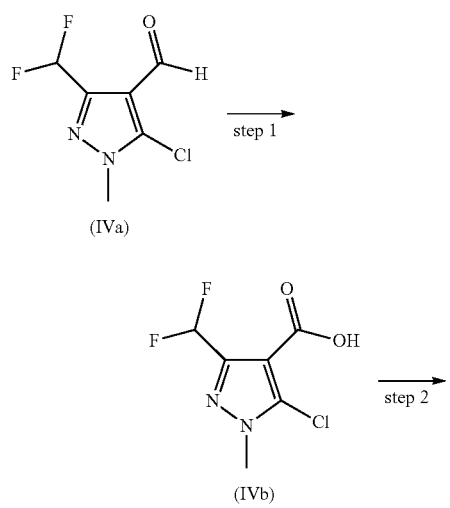

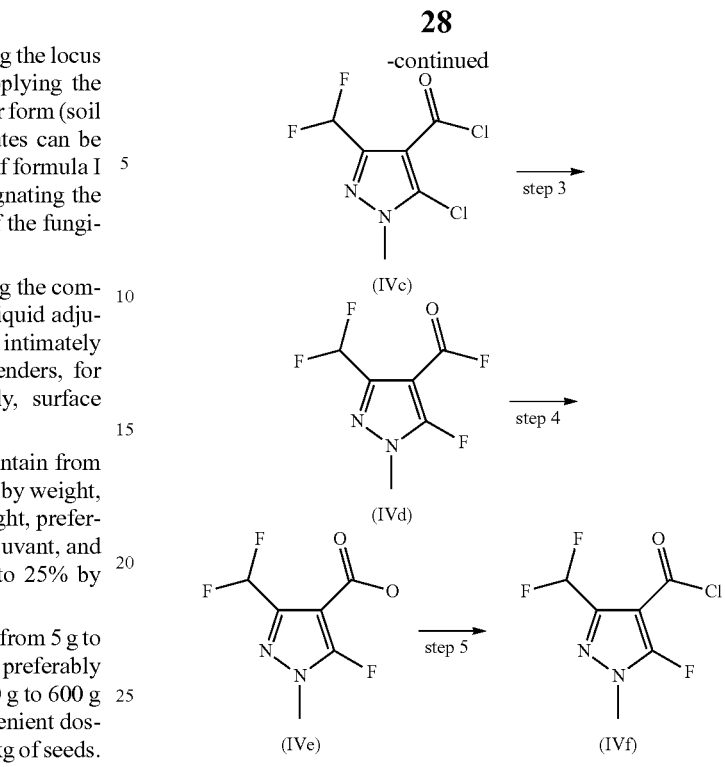

Process P1

5-chloro-3-(difluoromethyl)-1-methyl-1H-pyrazole-4-carbaldehyde according to formula (IVa) is known from WO-A 2004/014138 (reference example 35).

Step 1 of process P1 is performed in the presence of an oxidant, and if appropriate in the presence of a solvent.

Steps 2 and 5 of process P1 are performed in the presence of acid halide, and if appropriate in the presence of a solvent.

Step 3 of process P1 is performed in the presence of a fluorinating agent, and if appropriate in the presence of a solvent.

Step 4 of process P1 is performed in the presence of an acid or a base and if appropriate in the presence of a solvent Suitable oxidants for carrying out step of process P1 according to the invention are in each case all inorganic and organic oxidant which are customary for such reactions. Preference is given to using benzyltriethylammonium permanganate; bromine; chlorine; m-chloroperbenzoic acid; chromic acid; chromium (VI) oxide; hydrogen peroxide; hydrogen peroxide-boron trifluoride; hydrogen peroxide-urea; 2-hydroxyperoxyhexafluoro-2-propanol; Iodine; oxygen-platinum catalyst, perbenzoic acid; peroxyacetyl nitrate; potassium permanganate; potassium ruthenate; pyridinium dichromate; ruthenium (VIII) oxide; silver (I) oxide; silver (II) oxide; silver nitrite; sodium chlorite; sodium hypochlorite; 2,2,6,6-tetramethylpiperidin-1-oxyl.

Suitable acid halides for carrying out steps 2 and 5 of process P1 according to the invention are in each case all organic or inorganic acid halides which are customary for such reactions. Preference is given to using notably phosgene, phosphorous trichloride, phosphorous pentachloride, phosphorous trichloride oxide; thionyl chloride; or carbon tetrachloride-triphenylphosphine.

Suitable fluorinating agent for carrying out step 3 of process P1 according to the invention is in each case all fluorinating agents which are customary for such reactions. Preference is given to using cesium fluoride; potassium fluoride; potassium fluoride-calcium difluoride; tetrabutylammonium fluoride.

Suitable solvents for carrying out steps 1 to 5 of process P1 and process P2 according to the invention are in each case all customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decalin; chlorobenzene, dichlorobenzene, dichloromethane, chloroform, carbon tetrachloride, dichlorethane or trichlorethane; ethers, such as diethyl ether, cyclopentyl methylether, diisopropyl ether, methyl t-butyl ether, methyl t-amyl ether, dioxane, tetrahydrofuran, 2-methyl tetrahydrofuran, 1,2-dimethoxyethane, 1,2-diethoxyethane or anisole; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate, sulphoxides, such as dimethyl sulphoxide, or sulphones, such as sulpholane.

When carrying out steps 1 to 5 of process P1 or process P2 according to the invention, the reaction temperatures can independently be varied within a relatively wide range. Generally, processes according to the invention are carried out at temperatures between 0° C. and 160° C., preferably between 10° C. and 120° C. A way to control the temperature for the processes according to the invention is to use the microwaves technology.

Steps 1 to 5 of process P1 or process P2 according to the invention are generally independently carried out under atmospheric pressure. However, in each case, it is also possible to operate under elevated or reduced pressure.

When carrying out step 1 of process P1 according to the invention, generally 1 mol or other an excess of the oxidant is employed per mole of aldehyde of formula (IVa). It is also possible to employ the reaction components in other ratios.

When carrying out carrying out steps 2 and 5 of process P1 to the invention, generally 1 mol or other an excess of the acid halides is employed per mole of acid of formula (IVb) or (IVe). It is also possible to employ the reaction components in other ratios.

When carrying out steps 3 of process P1 according to the invention generally 1 mol or other an excess of fluorinating agent is employed per mole of acid (IVc). It is also possible to employ the reaction components in other ratios.

When carrying out steps 4 of process P1 according to the invention generally 1 mol or other an excess of acid or base is employed per mole of acid halides (IVd). It is also possible to employ the reaction components in other ratios.

Work-up is carried out by customary methods. Generally, the reaction mixture is treated with water and the organic phase is separated off and, after drying, concentrated under reduced pressure. If appropriate, the remaining residue can, be freed by customary methods, such as chromatography, recrystallization or distillation, from any impurities that may still be present.

Compounds according to the invention can be prepared according to the above described process. It will nevertheless be understood that, on the basis of his general knowledge and of available publications, the skilled worker will be able to adapt these processes according to the specifics of each of the compounds according to the invention that is desired to be synthesized.

The following examples illustrate in a non limiting manner the preparation and efficacy of the compounds of formula (I) according to the invention.

Example IVb

Synthesis of 5-chloro-3-(difluoromethyl)-1-methyl-1H-pyrazole-4-carboxylic acid

In a 500 ml flask, 6.0 g (31 mmol) of 5-chloro-3-(difluoromethyl)-1-methyl-1H-pyrazole-4-carbaldehyde were added to 30 ml of toluene. A solution of 2.4 g (62 mmol) of sodium hydroxide in 6 ml of water was added to the reaction mixture, followed by 103 ml of a 30% solution of hydrogen peroxide in water, whilst keeping the temperature below 37° C. After the end of the addition, the reaction mixture was stirred at 50° C. for 7 hours. Once the reaction mixture was back to room temperature, the two phases were separated and the organic phase was extracted with 100 ml of water. The combined aqueous phases were acidified to pH 2 with aqueous hydrochloric acid. The resulting white precipitate was filtered, washed two times with 20 ml of water, and dried to yield 3.2 g of 5-chloro-3-(difluoromethyl)-1-methyl-1H-pyrazole-4-carboxylic acid as a white solid.

$^1$H NMR (400 MHz, DMSO-d$_6$) δ ppm: 3.78 (s, 3H); 7.12 (t, 1H, J$_{HF}$=53.60 Hz) 13.19 (s, 1H);

IR (KBr): 1688 cm$^{-1}$ (C=O); 2200-3200 cm$^{-1}$ broad (hydrogen bond);

Example IVc

Synthesis of 5-chloro-3-(difluoromethyl)-1-methyl-1H-pyrazole-4-carbonyl chloride 3.2 g of 5-chloro-3-(difluoromethyl)-1-methyl-1H-pyrazole-4-carboxylic acid and 44.3 ml of thionyl chloride were refluxed for 5 hours. After cooling down, the reaction mixture was evaporated under vacuum to yield 3.5 g of 5-chloro-3-(difluoromethyl)-1-methyl-1H-pyrazole-4-carbonyl chloride as a yellow oil.

$^1$H NMR (400 MHz, CHCl$_3$-d$_6$) δ ppm: 3.97 (s, 3H); 7.00 (t, J=52.01 Hz, 1H);

IR (TQ): 1759 and 1725 cm$^{-1}$ (C=O);

Example IVd

Synthesis of 3-(difluoromethyl)-5-fluoro-1-methyl-1H-pyrazole-4-carbonyl fluoride To a dried solution of 4.0 g (70 mmol) of potassium fluoride in 21 ml of tetrahydrothiophene-1,1-dioxide was added a solution of 5.0 g (22 mmol) of 5-chloro-3-(difluoromethyl)-1-methyl-1H-pyrazole-4-carbonyl chloride in 15 ml of toluene at 100° C. The resulting reaction mixture was stirred at 190-200° C. for 22 hours. Distillation under vacuum yielded 8 g of a solution (25% molar) of 3-(difluoromethyl)-5-fluoro-1-methyl-1H-pyrazole-4-carbonyl fluoride in tetrahydrothiophene-1,1-dioxide.

$^1$H NMR (250 MHz, CHCl$_3$-d$_6$) δ ppm: 3.87 (s, 3H); 6.79 (t, J=53.75 Hz, 1H);

$^{19}$F NMR (250 MHz, CHCl$_3$-d$_6$) δ ppm: 45.37 (s, COF); −117.5 (d, J=28.2 Hz); −131.6 (m);

Example IVe

Synthesis of 5-fluoro-3-(difluoromethyl)-1-methyl-1H-pyrazole-4-carboxylic acid

To 400 ml of a 1N sodium hydroxide aqueous solution, was added dropwise 67.5 g of a solution (10% molar) of 3-(difluoromethyl)-5-fluoro-1-methyl-1H-pyrazole-4-carbonyl fluoride in tetrahydrothiophene 1,1-dioxide. The temperature was kept below 20° C. during the addition. After 2 hours of stirring at room temperature, the reaction mixture was carefully acidified to pH 2 with concentrated aqueous hydrochloric acid. The resulting white precipitate was filtered, washed with water, and dried to yield 6 g of 5-fluoro-3-(difluoromethyl)-1-methyl-1H-pyrazole-4-carboxylic acid as a white solid.

$^1$H NMR (400 MHz, DMSO-d$_6$) δ ppm: 3.90 (s, 3H); 7.22 (t, 1H, $J_{HF}$=53.55 Hz); 13.33 (s, 1H);

Example IVf

Synthesis of 5-fluoro-3-(difluoromethyl)-1-methyl-1H-pyrazole-4-carbonyl chloride 9.1 g of 5-fluoro-3-(difluoromethyl)-1-methyl-1H-pyrazole-4-carboxylic acid and 75.5 ml of thionyl chloride were refluxed for 1.5 hours. After cooling down, the reaction mixture was evaporated under vacuum to yield 10 g of 5-fluoro-3-(difluoromethyl)-1-methyl-1H-pyrazole-4-carbonyl chloride as a yellow oil.

GC-MS; observed M/z: Molecular ion: (M$^{+\cdot}$)=212; fragments: (M$^{+\cdot}$–Cl)=177 and (M$^{+\cdot}$–F)=193;

Educt for Example 1 and 2

Synthesis of 2-[1,1'-Bi(cyclopropyl)-2-yl]cyclohexanamine

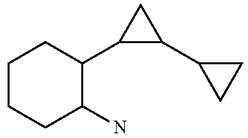 [SMILES: NC1CCCCC1C1CC1C1CC1]

0.289 g of Ru/C (5%) are added to a solution comprising 3.00 g (17.31 mmol) 2-[1,1'-Bi(cyclopropyl)-2-yl]anilin in 20 ml of tetrahydrofuran, and the mixture is hydrogenated with 100 bar of hydrogen at 120° C. for 20 hours. After cooling to room temperature, the catalyst is filtered off through Celite 545 and the product is concentrated under reduced pressure. This gives 3.01 g (96%) of 2-[1,1'-Bi(cyclopropyl)-2-yl]cyclohexanamine having a purity of 96% according to MSD-HPLC.

$^1$H NMR (600 MHz, CD3CN-d) δ ppm: 0.30-0.50 (m, 1H); 0.90-1.00 (m, 1H); 1.00-1.40 (m, 1H); 1.50-1.80 (m, 1H)

Example for the formation of compounds according to formula (I) as described in reaction scheme P1 outlined above:

Example 1 and 2

Synthesis of N-{2-[1,1'-bi(cyclopropyl)-2-yl]cyclohexyl}-3-(difluoromethyl)-5-fluoro-1-methyl-1H-pyrazole-4-carboxamide

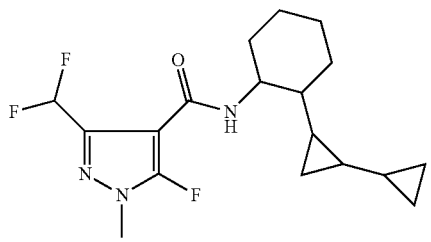 [SMILES: Cn1nc(C(F)F)c(C(=O)NC2CCCCC2C2CC2C2CC2)c1F]

To a mixture of 0.489 g (2.73 mmol) 2-[1,1'-bi(cyclopropyl)-2-yl]cyclohexanamine and 0.565 g (4.09 mmol) potassiumcarbonate in 30 ml Acetonitrile was added 0.638 g (3.00 mmol) 3-(difluoromethyl)-5-fluoro-1-methyl-1H-pyrazole-4-carbonyl chloride and stirred at ambient temperature overnight. At the end of the reaction the reaction mixture was extracted with ethylacetate and water. The organic layer was dried with natriumsulfate and the solvent was removed by vacuum. The crude product was purified by column chromathography (Solvent: Cyclohexane/ethylacetate gradient). Finally 0.40 g (33%) of N-{2-[1,1'-bi(cyclopropyl)-2-yl]cyclohexyl}-3-(difluoromethyl)-5-fluoro-1-methyl-1H-pyrazole-4-carboxamide with a purity of 87% LC-MS was isolated. logP (acid) of 4.02.

$^1$H NMR (400 MHz, DMSO-d) δ ppm: 0.1-0.90 (m, 1H); 1.00-1.90 (m, 1H); 1.70-1.80 (s, 1H); 7.00-7.40 (m, 1H)

Furtheron the following examples of compounds according to formula (I')

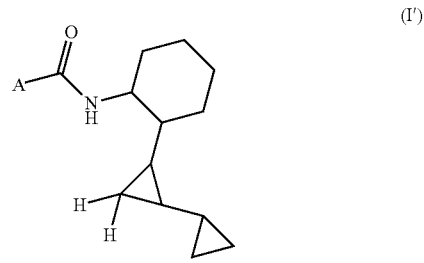

Are listed in table 1 with the following definitions:

TABLE 1

| Ex. | A | Isomer* |
|---|---|---|
| 1 | 3-(difluoromethyl)-5-fluoro-1-methyl-1H-pyrazol-4-yl | Isomer A |
| 2 | 3-(difluoromethyl)-5-fluoro-1-methyl-1H-pyrazol-4-yl | Isomer B (ex 1) (S) |
| 3 | 5-fluoro-1,3-dimethyl-1H-pyrazol-4-yl | |
| 4 | 5-chloro-3-(difluoromethyl)-1-methyl-1H-pyrazol-4-yl | |
| 5 | 1-methyl-3-(trifluoromethyl)-1H-pyrazol-4-yl | Racemic mixture of enantionmers and diastereomers |
| 6 | 2-methyl-4-(trifluoromethyl)-1,3-thiazol-5-yl | Racemic mixture of enantionmers and diastereomers |
| 7 | 2-(trifluoromethyl)phenyl | Racemic mixture of enantionmers and diastereomers |
| 8 | 2-chloropyridin-3-yl | |
| 9 | 5-fluoro-1,3-dimethyl-1H-pyrazol-4-yl | (S) |
| 10 | 5-chloro-3-(difluoromethyl)-1-methyl-1H-pyrazol-4-yl | (S) |
| 11 | 1-methyl-3-(trifluoromethyl)-1H-pyrazol-4-yl | (S) |
| 12 | 2-methyl-4-(trifluoromethyl)-1,3-thiazol-5-yl | (S) |
| 13 | 2-(trifluoromethyl)phenyl | (S) Isomer A of Ex 7 |
| 14 | 2-chloropyridin-3-yl | |
| 15 | 4-(difluoromethyl)-2-methyl-1,3-thiazol-5-yl | Isomer A |
| 16 | 4-(difluoromethyl)-2-methyl-1,3-thiazol-5-yl | Isomer B (ex 15) (S) |
| 17 | 3-(difluoromethyl)-1-methyl-1H-pyrazol-4-yl | (S) |
| 18 | 2-(trifluoromethyl)phenyl | Isomer B of Ex 7 |

Isomer A and B do represent different isosteromers of the same compound e.g. enantiomers and diastomers.

*chiral specification in the IUPAC-name at position 1 in the cyclohexyl-part of the examples:

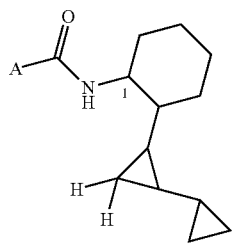

Throughout this description, temperatures are given in degrees Celsius; "NMR" means nuclear magnetic resonance spectrum; and "%" is percent by weight, unless corresponding concentrations are indicated in other units.

S=singlet br=broad d=doublet dd=doublet of doublets t=triplet q=quartet m=multiplet ppm=parts per million The NMR peaklist below shows selected NMR data of table 1, NMR-Data and Log P-Values of Selected Examples of Table 1
NMR-Peaklist Method 1H-NMR data of the selected examples of table 1 are written in form of 1H-NMR-peak lists. To each signal peak are listed the – value in ppm and the signal intensity:

Example 1

DMSO-d$_6$ 8.5569 (0.32) 7.5977 (0.36) 7.5726 (0.38) 7.5627 (0.39) 7.541 (0.36) 7.4122 (0.4) 7.3845 (0.43) 7.3522 (0.87) 7.332 (0.82) 7.2452 (0.49) 7.2076 (0.99) 7.1096 (0.98) 7.073 (1.91) 7.0542 (0.73) 7.031 (0.45) 6.9748 (0.54) 6.938 (0.99) 6.9192 (0.52) 4.1432 (1.46) 4.1219 (0.57) 4.1094 (0.61) 4.0996 (0.56) 4.0568 (1.72) 4.0391 (4.01) 4.0213 (3.81) 4.0033 (1.76) 3.8721 (0.46) 3.8068 (1.25) 3.7826 (10.98) 3.7435 (0.4) 3.7134 (0.39) 3.6865 (0.41) 3.6776 (0.41) 3.6429 (0.41) 3.62 (0.4) 3.4905 (0.81) 3.485 (1.08) 3.4716 (1.6) 3.4669 (1.3) 3.4491 (0.44) 3.4034 (0.65) 3.3066 (978.18) 3.2831 (21.01) 3.2387 (0.88) 3.1814 (1.55) 3.1639 (0.38) 3.0803 (0.38) 3.0691 (1.32) 2.9909 (5) 2.9687 (0.46) 2.9587 (0.48) 2.7855 (0.38) 2.6736 (1.26) 2.6692 (1.59) 2.6647 (1.18) 2.6327 (0.33) 2.5222 (7) 2.5089 (86.4) 2.5046 (157.8) 2.5002 (202.58) 2.4958 (140.65) 2.4917 (68.34) 2.3311 (1.1) 2.3269 (1.43) 2.3224 (1.07) 2.0689 (1.41) 2.0295 (0.42) 1.9867 (16) 1.9075 (0.48) 1.8317 (0.49) 1.8227 (0.52) 1.7688 (1.1) 1.7349 (1.23) 1.7066 (1.44) 1.6913 (1.51) 1.6384 (2.02) 1.6264 (2.22) 1.5892 (1.61) 1.5486 (1.5) 1.5273 (1.63) 1.5013 (2.11) 1.4871 (2.47) 1.476 (2.54) 1.4532 (2.12) 1.4448 (2.05) 1.4223 (2.16) 1.4049 (2.22) 1.3984 (3.22) 1.3676 (1.62) 1.3314 (1.43) 1.3156 (1.43) 1.2959 (1.89) 1.2659 (1.91) 1.2591 (1.83) 1.236 (1.88) 1.1928 (5.48) 1.175 (9.47) 1.1572 (5.32) 1.1077 (0.93) 1.0865 (0.83) 1.0713 (0.84) 1.0442 (0.57) 1.0142 (0.37) 0.9889 (0.34) 0.974 (0.34) 0.9642 (0.39) 0.9043 (0.95) 0.8894 (1.39) 0.8766 (1.67) 0.8606 (1.58) 0.8513 (1.52) 0.8349 (1.76) 0.8215 (1.02) 0.8105 (1.12) 0.7983 (1.05) 0.7906 (1.28) 0.7785 (1.27) 0.7661 (1.13) 0.7563 (1.09) 0.7432 (1.09) 0.7233 (0.95) 0.7082 (0.9) 0.6976 (1) 0.6883 (0.89) 0.6752 (0.84) 0.6212 (0.5) 0.5998 (0.65) 0.5655 (1.01) 0.561 (0.94) 0.5528 (1.23) 0.5418 (1.23) 0.532 (1.31) 0.5204 (1.12) 0.5091 (0.99) 0.5018 (0.95) 0.4967 (1.07) 0.4584 (1.88) 0.4485 (2.01) 0.4388 (1.99) 0.4261 (1.6) 0.4148 (1.53) 0.3853 (2.2) 0.3772 (1.75) 0.3676 (1.67) 0.3417 (1.36) 0.3249 (1.62) 0.2984 (1.51) 0.2922 (1.28) 0.288 (1.31) 0.2783 (1.33) 0.272 (1.41) 0.2451 (1.5) 0.2352 (1.33) 0.2244 (1.31) 0.2142 (1.44) 0.2026 (1.29) 0.193 (1.31) 0.1811 (1.37) 0.1688 (1.21) 0.1576 (1.37) 0.1461 (1.65) 0.1344 (1.59) 0.1224 (1.47) 0.1106 (1.5) 0.0992 (1.44) 0.0953 (1.44) 0.0869 (1.21) 0.0736 (1.11) 0.0634 (0.99) 0.0505 (0.85) 0.0376 (0.86) 0.0078 (2.36) –0.0002 (29.16) –0.0086 (2.16) –0.0142 (1.55) –0.0271 (2.26) –0.0403 (2.67) –0.0538 (2.05) –0.0985 (0.39) –0.1124 (0.35) –0.124 (0.38) –0.1308 (0.4) –0.1495 (0.41)
Log P[b]=4.02

Example 2

DMSO-d$_6$ 7.5946 (0.49) 7.5611 (1.37) 7.5386 (1.46) 7.3478 (0.39) 7.3255 (0.41) 7.2449 (1.68) 7.216 (0.41) 7.2103 (0.55) 7.1544 (0.39) 7.1101 (3.7) 7.0809 (0.89) 7.0756 (1.22) 6.9754 (1.9) 6.9458 (0.49) 6.9409 (0.66) 3.8056 (1.55) 3.7831 (16) 3.6675 (0.51) 3.657 (0.49) 3.6412 (0.82) 3.6181 (0.83) 3.5928 (0.43) 3.3052 (288.59) 2.6738 (0.45) 2.6693 (0.56) 2.6646 (0.46) 2.5223 (2.75) 2.5089 (30.03) 2.5047 (53.84) 2.5002 (68.38) 2.4959 (47.25) 2.3314 (0.42) 2.3269 (0.54) 2.3223 (0.39) 2.0692 (0.57) 2.0343 (0.41) 1.7683 (1.77) 1.7404 (2.19) 1.7089 (1.42) 1.6455 (2.68) 1.6263 (2.15) 1.5516 (0.44) 1.5011 (0.77) 1.4763 (0.86) 1.4469 (0.72) 1.4295 (0.61) 1.421 (0.69) 1.3994 (0.69) 1.3829 (0.59) 1.3549 (0.6) 1.3171 (0.85) 1.2953 (1.4) 1.2615 (1.49) 1.2419 (2.03) 1.2225 (2.07) 1.1962 (1.1) 1.1642 (0.95) 1.1466 (1.18) 1.133 (1.07) 1.1077 (1.34) 1.0861 (1.66) 1.0677 (1.73) 1.0385 (0.8) 1.0093 (0.32) 0.9052 (0.43) 0.8775 (2.01) 0.8614 (1.99) 0.8516 (0.74) 0.8451 (0.5) 0.8351 (0.72) 0.8183 (0.35) 0.7877 (0.51) 0.7753 (0.81) 0.7639 (1.07) 0.7546 (1.44) 0.7433 (1.62) 0.7344 (1.15) 0.723 (1.28) 0.7101 (0.88) 0.6974 (1.1) 0.6755 (0.98) 0.6499 (0.44) 0.5825 (0.52) 0.5791 (0.54) 0.5674 (0.65) 0.5519 (0.62) 0.5449 (0.52) 0.5312 (0.58) 0.5185 (0.54) 0.5104 (0.43) 0.4974 (0.49) 0.4698 (1.25) 0.46 (1.99) 0.4496 (2.33) 0.4393 (2.66) 0.4279 (2.06) 0.4164 (1.29) 0.3979 (1.79) 0.3876 (2.9) 0.3768 (2.16) 0.3665 (1.88) 0.3553 (1.11) 0.3459 (1.14) 0.3419 (1.09) 0.3255 (1.06) 0.3102 (0.68) 0.3065 (0.72) 0.2982 (1.05) 0.2877 (1.59) 0.2835 (1.58) 0.2793 (1.85) 0.2688 (2.23) 0.2626 (2.1) 0.2586 (1.97) 0.2531 (2.1) 0.2488 (2.16) 0.2454 (2.03) 0.2414 (1.64) 0.2379 (1.64) 0.2264 (1.35) 0.2152 (1.21) 0.2044 (0.6) 0.1813 (0.44) 0.1679 (1.38) 0.1573 (1.98) 0.1459 (2.08) 0.1353 (1.63) 0.124 (1.15) 0.1117 (0.96) 0.0996 (0.88) 0.0952 (0.93) 0.0868 (0.8) 0.0826 (0.79) 0.074 (0.72) 0.0641 (0.5) 0.0598 (0.55) 0.0512 (0.43) 0.0078 (1.61) –0.0002 (14.28) –0.0086 (1.09) –0.0236 (1.13) –0.0335 (1.57) –0.0421 (2.28) –0.0458 (2.24) –0.0501 (1.78) –0.0546 (2.17) –0.0586 (2.15) –0.063 (1.96) –0.0674 (1.55) –0.0712 (1.2) –0.0762 (1.43) –0.08 (0.97) –0.0889 (0.66) –0.099 (0.41)
Log P[b]=3.84

Example 3

DMSO-d$_6$ 17.143 (1.82) 12.9084 (1.73) 11.8878 (1.65) 10.4516 (1.7) 7.1746 (1.58) 4.6724 (1.62) 4.0736 (1.66) 4.0444 (1.89) 3.9636 (1.94) 3.939 (2.1) 3.9252 (1.76) 3.915 (1.76) 3.8709 (1.72) 3.8503 (1.71) 3.8239 (2.1) 3.7951 (2.34) 3.7736 (1.83) 3.7384 (2.18) 3.7318 (2.45) 3.6729 (2.74) 3.6588 (3.03) 3.6379 (6.8) 3.6236 (10) 3.5929 (2.92) 3.5634 (3.22) 3.5568 (3.01) 3.5428 (3.88) 3.4832 (4.52) 3.4725 (4.86) 3.4543 (5.1) 3.4276 (7.01) 3.4167 (7.3) 3.2789 (172.82) 3.2392 (3.96) 3.2233 (2.75) 3.1953 (1.72) 2.719 (1.84) 2.7076 (2.17) 2.6984 (2.26) 2.6734 (12.47) 2.669 (16) 2.6646 (12.2) 2.6442

(3.39) 2.6158 (3.41) 2.5389 (191.96) 2.5086 (920.07) 2.5043
(1696.22) 2.4998 (2192.31) 2.4954 (1505.29) 2.491 (708.35)
2.4192 (1.84) 2.3311 (10.26) 2.3266 (13.69) 2.3219 (9.62)
2.2408 (6.8) 2.2204 (9.16) 2.0692 (15.55) 1.7732 (1.77)
1.6698 (1.65) 1.6426 (1.88) 1.6349 (2.2) 1.6049 (1.67)
1.2342 (5.11) 1.2083 (2.53) 1.2036 (2.57) 1.0639 (2.21) 1.06
(1.89) 0.7222 (1.7) 0.2712 (1.76) 0.2508 (1.71) 0.2458 (1.9)
0.1515 (2.49) 0.1458 (6.52) 0.1139 (1.63) 0.087 (1.88)
0.0079 (65.62) −0.0002 (1338.36) −0.0085 (51.19) −0.0414
(2.57) −0.0558 (1.84) −0.1494 (5.95)

Log P[b]=3.35

Example 5

DMSO-d$_6$ 8.3021 (3.64) 8.2862 (0.81) 8.2575 (0.6) 8.2304 (0.53)
8.2087 (3.19) 7.903 (0.33) 7.8805 (0.45) 7.8652 (0.36)
7.8385 (1.43) 7.8164 (1.64) 7.8078 (1.69) 7.7838 (1.28)
7.6453 (0.34) 4.1151 (0.34) 4.1062 (0.36) 4.0514 (0.33)
4.0128 (0.43) 3.9996 (0.49) 3.9491 (15.4) 3.9299 (16) 3.8945
(0.4) 3.8772 (0.33) 3.8582 (0.39) 3.8441 (0.36) 3.8323 (0.35)
3.808 (0.4) 3.7715 (0.56) 3.7613 (0.51) 3.7479 (0.57) 3.7256
(0.49) 3.7175 (0.49) 3.7115 (0.49) 3.6853 (0.79) 3.6576
(1.31) 3.6452 (1.23) 3.635 (1.71) 3.6085 (1.31) 3.5078 (0.87)
3.4628 (1.07) 3.459 (1.06) 3.4434 (1.24) 3.388 (2.3) 3.3048
(3501.04) 3.2811 (36.88) 2.795 (0.33) 2.7101 (0.58) 2.6734
(2.48) 2.669 (3.11) 2.6647 (2.36) 2.6372 (0.59) 2.6239 (0.71)
2.5391 (87.31) 2.5088 (178.89) 2.5044 (334.85) 2.4999
(439.78) 2.4955 (306.74) 2.4911 (148.29) 2.4191 (0.38)
2.3635 (0.36) 2.3312 (2.15) 2.3267 (2.74) 2.3222 (2.04)
2.0692 (3.89) 1.8015 (0.54) 1.745 (2.75) 1.7358 (2.7) 1.6838
(1.76) 1.6533 (3.07) 1.6281 (2) 1.5787 (0.35) 1.5544 (0.36)
1.3768 (0.39) 1.3542 (0.36) 1.333 (0.35) 1.3041 (0.63) 1.298
(0.68) 1.282 (0.94) 1.2367 (2.5) 1.2135 (2.01) 1.2054 (2.08)
1.1866 (1.89) 1.1565 (1.82) 1.1264 (1.32) 1.082 (2.31)
1.0693 (2.55) 1.0389 (1.25) 0.9291 (0.35) 0.9134 (0.39)
0.9001 (0.97) 0.8895 (1.2) 0.8767 (1.08) 0.8667 (1.1) 0.8543
(0.7) 0.7733 (0.43) 0.7595 (0.67) 0.7512 (0.96) 0.7403 (0.99)
0.7299 (0.66) 0.7196 (0.49) 0.7003 (0.37) 0.6596 (1.55)
0.6466 (1.49) 0.6374 (2.38) 0.6265 (2.36) 0.6165 (1.61)
0.6071 (1.58) 0.5864 (0.66) 0.5655 (0.39) 0.5179 (0.37)
0.4929 (0.35) 0.456 (0.74) 0.4447 (1.05) 0.4341 (1.52)
0.4233 (1.52) 0.4149 (1.33) 0.4041 (1.42) 0.3945 (1.41)
0.3872 (0.72) 0.3729 (0.57) 0.3578 (0.4) 0.3139 (1.06)
0.2923 (1.15) 0.2739 (1.43) 0.2684 (1.45) 0.2614 (1.94)
0.2484 (1.73) 0.2406 (1.99) 0.2287 (1.92) 0.218 (1.8) 0.2063
(1.7) 0.1946 (1.08) 0.1836 (0.81) 0.1717 (0.52) 0.1463 (0.51)
0.132 (0.97) 0.1224 (1.33) 0.1117 (1.43) 0.0952 (1.26)
0.0869 (1.22) 0.0818 (1.33) 0.0744 (1.6) 0.0692 (1.3) 0.0616
(1.87) 0.0546 (1.27) 0.0491 (1.79) 0.0378 (1.22) 0.0285 (1.3)
0.0079 (3.86) −0.0002 (64.29) −0.0084 (3.3) −0.0166 (2.44)
−0.0238 (1.97) −0.0314 (2.05) −0.0376 (2.26) −0.0511 (2.12)
−0.0637 (1.69) −0.0678 (1.88) −0.0718 (1.83) −0.0852 (1.54)
−0.0962 (0.77) −0.1076 (0.61) −0.1322 (0.47) −0.1541 (1.06)
−0.1667 (1.25) −0.1753 (1.42) −0.1874 (0.85) −0.1992 (0.8)
−0.2116 (1.29) −0.2209 (1.4) −0.2247 (1.14) −0.2327 (0.84)
−0.2482 (0.52) −0.3227 (0.43) −2.8999 (0.32) −3.0829 (0.37)

Log P[b]=3.61

Example 6

CD$_3$CN 2.7001 (2.53) 2.6907 (1.85) 2.5149 (16) 2.2989 (23.27)
1.9534 (0.9) 1.9493 (1.64) 1.9452 (2.39) 1.9411 (1.64) 1.937
(0.83) 0.9226 (0.42) −0.0002 (0.79)

Log P[b]=4.14

Example 7

CD$_3$CN 7.7573 (6.09) 7.7565 (6.62) 7.7557 (6.2) 7.7426 (12.09)
7.7337 (1.83) 7.7286 (6.42) 7.6925 (2.29) 7.6916 (2.29)
7.6798 (6.62) 7.6729 (3.24) 7.6719 (3.16) 7.6677 (6.14)
7.6667 (5.89) 7.6603 (7.02) 7.6594 (6.65) 7.6476 (11.52)
7.6465 (12.11) 7.6348 (4.11) 7.6338 (4.19) 7.6123 (3.19)
7.611 (4.12) 7.6099 (3.81) 7.6087 (3.03) 7.5976 (8.44)
7.5964 (8.03) 7.5844 (6.36) 7.5831 (6.85) 7.5766 (0.66)
7.5716 (1.72) 7.5701 (2.14) 7.5283 (5.5) 7.5275 (5.95)
7.5159 (4.64) 7.5149 (5.03) 7.4831 (1.25) 7.4705 (1.08)
6.724 (1.84) 6.7119 (1.97) 6.6794 (1.78) 6.6657 (1.58)
3.7905 (1.13) 3.7838 (1.21) 3.7749 (1.46) 3.7721 (1.93)
3.7684 (1.69) 3.766 (1.95) 3.7568 (3.22) 3.7543 (2) 3.7501
(3.35) 3.742 (1.87) 3.7389 (3.79) 3.7354 (2.21) 3.7323 (3.68)
3.7243 (2.52) 3.7213 (2.02) 3.7177 (2.61) 3.7147 (1.75)
3.7067 (1.48) 3.6999 (1.39) 3.6033 (0.41) 3.5966 (0.43)
3.5874 (0.48) 3.5812 (0.45) 3.2762 (0.36) 3.2677 (0.36)
2.5074 (6.23) 2.2571 (1.01) 2.2315 (896.74) 2.2075 (1.55)
2.0573 (0.48) 2.0532 (0.73) 2.0491 (0.51) 2.002 (0.81) 1.996
(2.11) 1.9935 (2.23) 1.9899 (2.34) 1.9873 (2.33) 1.981 (1.71)
1.9747 (2.36) 1.9723 (2.52) 1.9669 (5.89) 1.9588 (4.29)
1.9547 (4.77) 1.9508 (44.96) 1.9468 (87.64) 1.9427 (126.66)
1.9386 (82.88) 1.9344 (41.23) 1.9298 (1.85) 1.9255 (1.56)
1.9227 (1.98) 1.9203 (1.98) 1.9167 (1.96) 1.9142 (2.01)
1.9105 (1.01) 1.9079 (1.43) 1.905 (1.03) 1.9016 (1.94)
1.8992 (2.07) 1.8955 (2.04) 1.8931 (1.97) 1.887 (0.77)
1.8788 (0.46) 1.8756 (0.5) 1.8732 (0.49) 1.87 (0.47) 1.8569
(0.45) 1.8536 (0.51) 1.8514 (0.49) 1.848 (0.46) 1.8361 (0.44)
1.832 (0.68) 1.8279 (1.29) 1.8237 (1.42) 1.8196 (1.59)
1.8171 (1.98) 1.8135 (1.94) 1.8113 (1.81) 1.8067 (2.03)
1.7971 (3.63) 1.7912 (3.31) 1.7875 (3.04) 1.7854 (2.94)
1.781 (3.07) 1.7744 (2.94) 1.7714 (2.59) 1.7684 (1.7) 1.7655
(1.91) 1.761 (0.89) 1.7572 (0.62) 1.7532 (0.73) 1.7456 (0.91)
1.7399 (0.89) 1.7361 (1.1) 1.7306 (1) 1.7267 (1.49) 1.7238
(2.02) 1.7211 (2.38) 1.7181 (3.13) 1.7125 (3.26) 1.7097
(3.13) 1.7072 (3.58) 1.7017 (4) 1.6957 (4.72) 1.6909 (5.7)
1.6871 (5.77) 1.6851 (5.67) 1.6827 (6.08) 1.6791 (5.62)
1.6734 (4.61) 1.6704 (4.34) 1.6672 (4.21) 1.664 (4.49)
1.6615 (3.82) 1.6581 (2.77) 1.6555 (2.25) 1.6495 (0.76)
1.6461 (0.55) 1.6397 (0.4) 1.3861 (0.5) 1.3843 (0.57) 1.3783
(0.94) 1.3735 (0.96) 1.3685 (1.23) 1.3628 (2.21) 1.3568
(2.93) 1.3521 (2.67) 1.3471 (3.1) 1.3415 (3.24) 1.3358 (3.44)
1.3303 (3.31) 1.3265 (2.75) 1.3213 (2.53) 1.315 (1.81)
1.3111 (1.55) 1.3089 (1.61) 1.3053 (1.44) 1.2975 (0.74)
1.2897 (0.83) 1.2821 (0.67) 1.2766 (0.66) 1.2729 (1.07) 1.27
(1.39) 1.265 (0.77) 1.2616 (1.07) 1.2575 (1.17) 1.2541 (0.86)
1.2479 (0.82) 1.2453 (0.67) 1.2413 (0.89) 1.2367 (0.53)
1.2326 (0.8) 1.2301 (0.95) 1.2263 (1.01) 1.2194 (0.51)
1.2106 (0.9) 1.2051 (2.04) 1.1991 (2.76) 1.1936 (2.39)
1.1837 (4.46) 1.179 (7.14) 1.1724 (5.52) 1.1662 (7.84)
1.1617 (8.66) 1.1599 (9.5) 1.1535 (10.37) 1.1476 (10.7)
1.1429 (6.07) 1.1387 (5.69) 1.1329 (5.69) 1.1266 (5.08)
1.1173 (0.63) 1.1125 (1.89) 1.1061 (1.08) 1.1009 (0.68)
1.0742 (0.4) 1.0683 (0.4) 1.0553 (0.36) 1.0525 (0.64) 1.0497
(0.43) 1.0467 (0.57) 1.0338 (0.48) 1.0308 (0.4) 1.028 (0.48)
0.8986 (1.3) 0.8912 (3.78) 0.8838 (5.31) 0.8813 (2.95)
0.8791 (3.65) 0.8765 (6.26) 0.8727 (4.31) 0.8677 (6.08)
0.8654 (3.36) 0.8624 (2.94) 0.86 (4.21) 0.8548 (3.06) 0.8526
(1.66) 0.8471 (2.1) 0.8391 (0.83) 0.8162 (0.68) 0.808 (1.96)
0.8025 (1.61) 0.7998 (2.19) 0.7944 (4.13) 0.7917 (1.23)
0.7889 (1.23) 0.7862 (4.33) 0.7808 (2.33) 0.778 (1.8) 0.7727
(2.26)

Log P[b]=4.11

Example 13

Isomer A

Log P[b]=4.17
M+H=352.19

Example 15

Log P[b]=4.31
M+H=357.30

Example 18

Isomer B

Log P[b]=4.23
M+H=352.24

Intensity of sharp signals correlates with the height of the signals in a printed example of a NMR spectrum in cm and shows the real relations of signal intensities. From broad signals several peaks or the middle of the signal and their relative intisity in comparison to the most intensive signal in the spectrum can be shown The 1H-NMR peak lists are similar to classical 1H-NMR prints and contain therefore usually all peaks, which are listed at classical NMR-interpretation.

Additionally they can show like classical 1H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$d_6$ and the peak of water are shown in our 1H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical 1H-NMR interpretation.

Measurement of log P values was performed according EEC directive 79/831 Annex V.A8 by HPLC (High Performance Liquid Chromatography) on reversed phase columns with the following methods:

[b] measurement of LC-MS was done at pH 2.7 with 0.1% formic acid in water and with acetonitrile (contains 0.1% formic acid) as eluent with a linear gradient from 10% acetonitrile to 95% acetonitrile.

Calibration was done with not branched alkan2-ones (with 3 to 16 carbon atoms) with known log P-values (measurement of log P values using retention times with linear interpolation between successive alkanones). lambda-maX-values were determined using UV-spectra from 200 nm to 400 nm and the peak values of the chromatographic signals.

In table 1, M+H (or M H) means the molecular ion peak, plus or minus 1 a.m.u. (atomic mass unit) respectively, as observed in mass spectroscopy and M (ApcI+) means the molecular ion peak as it was found via positive atmospheric pressure chemical ionisation in mass spectroscopy.

*Sphaerotheca* Test (Cucumber)/Preventive

Solvent: 49 parts by weight of N,N-Dimethylformamide
Emulsifier: 1 part by weight of Alkylarylpolyglycolether To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. One day after this treatment, the plants are inoculated with an aqueous spore suspension of *Sphaerotheca fuliginea*. Then the plants are placed in a greenhouse at approximately 23° C. and a relative atmospheric humidity of approximately 70%.

The test is evaluated 7 days after the inoculation. 0% means an efficacy which corresponds to that of the untreated control, while an efficacy of 100% means that no disease is observed.

In this test the following compounds according to the invention showed efficacy of 70% or even higher at a concentration of 500 ppm of active ingredient.

| Example # | Eff. % |
|---|---|
| 1 | 100 |
| 2 | 100 |
| 3 | 95 |
| 4 | 100 |
| 5 | 90 |
| 6 | 94 |
| 7 | 78 |

*Alternaria* Test (Tomato)/Preventive

Solvent: 49 parts by weight of N,N-Dimethylformamide
Emulsifier: 1 part by weight of Alkylarylpolyglycolether To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. One day after this treatment, the plants are inoculated with an aqueous spore suspension of *Alternaria solani*. The plants remain for one day in an incubation cabinet at approximately 22° C. and a relative atmospheric humidity of 100%. Then the plants are placed in an incubation cabinet at approximately 20° C. and a relative atmospheric humidity of 96%.

The test is evaluated 7 days after the inoculation. 0% means an efficacy which corresponds to that of the untreated control while an efficacy of 100% means that no disease is observed.

In this test the following compounds according to the invention showed efficacy of 70% or even higher at a concentration of 500 ppm of active ingredient.

| Example # | Eff. % |
|---|---|
| 1 | 100 |
| 2 | 100 |
| 3 | 94 |
| 4 | 95 |

-continued

| Example # | Eff. % |
|---|---|
| 5 | 94 |
| 6 | 94 |

*Pyrenophora* Test (Barley)/Preventive

Solvent: 49 parts by weight of N,N-Dimethylformamide

Emulsifier: 1 part by weight of Alkylarylpolyglycolether

To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. One day after this treatment, the plants are inoculated with an aqueous spore suspension of *Pyrenophora teres*. The plants remain for 48 hours in an incubation cabinet at 22° C. and a relative atmospheric humidity of 100%. Then the plants are placed in a greenhouse at a temperature of approximately 20° C. and a relative atmospheric humidity of approximately 80%.

The test is evaluated 7-9 days after the inoculation. 0% means an efficacy which corresponds to that of the untreated control while an efficacy of 100% means that no disease is observed.

In this test the following compounds according to the invention showed efficacy of 70% or even higher at a concentration of 500 ppm of active ingredient.

| Example # | Eff. % |
|---|---|
| 1 | 100 |
| 2 | 100 |
| 3 | 100 |
| 4 | 80 |
| 5 | 95 |
| 6 | 100 |
| 8 | 90 |
| 7 | 90 |

*Podosphaera* Test (Apples)/Preventive

Solvent: 24.5 parts by weight of acetone
24.5 parts by weight of dimethylacetamide Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. After the spray coating has dried on, the plants are inoculated with an aqueous spore suspension of the causal agent of apple mildew (*Podosphaera leucotricha*). The plants are then placed in a greenhouse at approximately 23° C. and a relative atmospheric humidity of approximately 70%.

The test is evaluated 10 days after the inoculation. 0% means an efficacy which corresponds to that of the untreated control, while an efficacy of 100% means that no disease is observed.

In this test the following compounds according to the invention showed efficacy of 70% or even higher at a concentration of 100 ppm of active ingredient.

| Example # | Eff. % |
|---|---|
| 1 | 100 |
| 2 | 100 |

*Venturia* Test (Apples)/Preventive

Solvent: 24.5 parts by weight of acetone
24.5 parts by weight of dimethylacetamide Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. After the spray coating has dried on, the plants are inoculated with an aqueous conidia suspension of the causal agent of apple scab (*Venturia inaequalis*) and then remain for 1 day in an incubation cabinet at approximately 20° C. and a relative atmospheric humidity of 100%.

The plants are then placed in a greenhouse at approximately 21° C. and a relative atmospheric humidity of approximately 90%.

The test is evaluated 10 days after the inoculation. 0% means an efficacy which corresponds to that of the untreated control, while an efficacy of 100% means that no disease is observed.

In this test the following compounds according to the invention showed efficacy of 70% or even higher at a concentration of 100 ppm of active ingredient.

| Example # | Eff. % |
|---|---|
| 1 | 100 |
| 2 | 100 |

*Blumeria* Test (Barley)/Preventive

Solvent: 49 parts by weight of n,n-dimethylacetamid

Emulsifier: 1 part by weight of alkylaryl polyglycol ether

To produce a suitable preparation of active compound, 1 part by weight of active compound or active compound combination is mixed with the stated amounts of solvent and emulsifier, and the concentrate is diluted with water to the desired concentration.

To test for preventive activity, young plants are sprayed with the preparation of active compound or active compound combination at the stated rate of application.

After the spray coating has been dried, the plants are dusted with spores of *Blumeria graminis* f.sp. hordei.

The plants are placed in the greenhouse at a temperature of approximately 18° C. and a relative atmospheric humidity of approximately 80% to promote the development of mildew pustules.

The test is evaluated 7 days after the inoculation. 0% means an efficacy which corresponds to that of the untreated control, while an efficacy of 100% means that no disease is observed.

In this test the following compounds according to the invention showed an efficacy of 70% or even higher at a concentration of 500 ppm of active ingredient.

| Example # | Eff. % |
|---|---|
| 1 | 100 |
| 2 | 100 |

*Septoria tritici*-Test (Wheat)/Preventive
Solvent: 49 parts by weight of n,n-dimethylacetamid
Emulsifier: 1 part by weight of alkylaryl polyglycol ether To produce a suitable preparation of active compound, 1 part by weight of active compound or active compound combination is mixed with the stated amounts of solvent and emulsifier, and the concentrate is diluted with water to the desired concentration.

To test for preventive activity, young plants are sprayed with the preparation of active compound or active compound combination at the stated rate of application.

After the spray coating has been dried, the plants are sprayed with a spore suspension of *Septoria tritici*. The plants remain for 48 hours in an incubation cabinet at approximately 20° C. and a relative atmospheric humidity of approximately 100% and afterwards for 60 hours at approximately 15° C. in a translucent incubation cabinet at a relative atmospheric humidity of approximately 100%.

The plants are placed in the greenhouse at a temperature of approximately 15° C. and a relative atmospheric humidity of approximately 80%.

The test is evaluated 21 days after the inoculation. 0% means an efficacy which corresponds to that of the untreated control, while an efficacy of 100% means that no disease is observed.

In this test the following compounds according to the invention showed an efficacy of 70% or even higher at a concentration of 500 ppm of active ingredient.

| Example # | Eff. % |
|---|---|
| 1 | 90 |
| 2 | 90 |

*Puccinia triticina*-Test (Wheat)/Preventive
Solvent: 49 parts by weight of n,n-dimethylacetamid
Emulsifier: 1 part by weight of alkylaryl polyglycol ether To produce a suitable preparation of active compound, 1 part by weight of active compound or active compound combination is mixed with the stated amounts of solvent and emulsifier, and the concentrate is diluted with water to the desired concentration.

To test for preventive activity, young plants are sprayed with the preparation of active compound or active compound combination at the stated rate of application.

After the spray coating has been dried, the plants are sprayed with a spore suspension of *Puccinia triticina*. The plants remain for 48 hours in an incubation cabinet at approximately 20° C. and a relative atmospheric humidity of approximately 100%.

The plants are placed in the greenhouse at a temperature of approximately 20° C. and a relative atmospheric humidity of approximately 80%.

The test is evaluated 8 days after the inoculation. 0% means an efficacy which corresponds to that of the untreated control, while an efficacy of 100% means that no disease is observed.

In this test the following compounds according to the invention showed an efficacy of 70% or even higher at a concentration of 500 ppm of active ingredient.

| Example # | Eff. % |
|---|---|
| 1 | 100 |
| 2 | 100 |

*Fusarium nivale* (var. *majus*)-Test (Wheat)/Preventive
Solvent: 49 parts by weight of n,n-dimethylacetamid
Emulsifier: 1 part by weight of alkylaryl polyglycol ether To produce a suitable preparation of active compound, 1 part by weight of active compound or active compound combination is mixed with the stated amounts of solvent and emulsifier, and the concentrate is diluted with water to the desired concentration.

To test for preventive activity, young plants are sprayed with the preparation of active compound or active compound combination at the stated rate of application.

After the spray coating has been dried, the plants are slightly injured by using a sandblast and afterwards they are sprayed with a conidia suspension of *Fusarium nivale* (var. *majus*).

The plants are placed in the greenhouse under a translucent incubation cabinet at a temperature of approximately 10° C. and a relative atmospheric humidity of approximately 100%.

The test is evaluated 5 days after the inoculation. 0% means an efficacy which corresponds to that of the untreated control, while an efficacy of 100% means that no disease is observed.

In this test the following compounds according to the invention showed an efficacy of 70% or even higher at a concentration of 500 ppm of active ingredient.

| Example # | Eff. % |
|---|---|
| 1 | 100 |
| 2 | 100 |

The invention claimed is:

1. A compound of formula (IV)

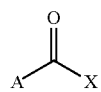

(IV)

in which
A represents A1 below

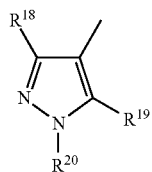

A1

$R^{18}$ is difluoromethyl or dichloromethyl, $R^{19}$ is fluorine or chlorine, and $R^{20}$ is methyl and X is hydroxyl or halogen.

2. The compound of claim 1, wherein X is hydroxyl.
3. The compound of claim 1, wherein X is halogen.
4. The compound of claim 1, wherein $R^{19}$ is fluorine.
5. The compound of claim 1, wherein $R^{19}$ is chlorine.
6. The compound of claim 1, wherein $R^{18}$ is difluoromethyl.
7. The compound of claim 1, wherein $R^{18}$ is dichloromethyl.

* * * * *